(12) United States Patent
Goping

(10) Patent No.: US 8,447,783 B2
(45) Date of Patent: May 21, 2013

(54) INTELLIGENT AGENT AND MANAGER SYSTEM

(75) Inventor: Ing Han Frank Goping, Mississauga (CA)

(73) Assignee: Laborie Medical Technologies Canada ULC, Mississauga, Ontario (CA)

( * ) Notice: Subject to any disclaimer, the term of this patent is extended or adjusted under 35 U.S.C. 154(b) by 34 days.

(21) Appl. No.: 13/106,857

(22) Filed: May 13, 2011

(65) Prior Publication Data

US 2012/0124022 A1 May 17, 2012

Related U.S. Application Data

(60) Provisional application No. 61/349,557, filed on May 28, 2010.

(51) Int. Cl.
*G06F 17/30* (2006.01)

(52) U.S. Cl.
USPC ............ 707/791; 707/802; 707/822; 707/828

(58) Field of Classification Search
USPC ................................................ 707/600–899
See application file for complete search history.

(56) References Cited

U.S. PATENT DOCUMENTS

| | | | |
|---|---|---|---|
| 6,122,664 A | 9/2000 | Boukobza et al. | |
| 7,330,842 B2 | 2/2008 | Sleat | |
| 7,386,522 B1 * | 6/2008 | Bigus et al. | 706/15 |
| 2003/0167249 A1 | 9/2003 | Park | |
| 2005/0010544 A1 | 1/2005 | Sleat | |
| 2006/0106745 A1 | 5/2006 | Armstrong et al. | |

* cited by examiner

*Primary Examiner* — Isaac M Woo
(74) *Attorney, Agent, or Firm* — Cahn & Samuels, LLP

(57) ABSTRACT

A system having an agent manager and a plurality of agents for assisting a user in reaching a conclusion is provided in at least one embodiment. In at least one embodiment, the system is in communication with at least one database housing information to be analyzed by at least one of the agents. Further embodiments include the operation of the system and its interaction with the at least one database. In at least one further embodiment, the method includes the development and publication of the agents.

19 Claims, 20 Drawing Sheets

| N | Agent Name | Progression | Status | Favorite | Output |
|---|---|---|---|---|---|
| 1 | PNE to screen for... | 75% | Wait For DB l... | No | |
| 3 | Bladder Necrosis | 33% | Wait For DB l... | No | Paper does not apply. |
| 4 | Female SUI MUS... | 0% | Finished | No | |
| 5 | Do women with p... | 66% | Wait For DB l... | No | Paper does not apply Gender restriction. |
| 6 | TURis-PVP vs. st... | 0% | Finished | No | |
| 7 | Antimuscarinics a... | 0% | Finished | No | Paper does not apply Gender restriction. |
| 8 | Preop MUS Valsa... | 66% | Wait For DB l... | No | |
| 9 | Reevaluating Occ... | 50% | Wait For DB l... | No | Paper does not apply. |
| 10 | Sacral Neuromod... | 0% | Finished | No | |
| 11 | Incontinence and... | 0% | Wait For DB l... | No | |
| 12 | Incontinence and... | 100% | Finished | No | |
| 13 | Pharma treatmen... | 100% | Finished | No | |
| 14 | Vaginal wall sling... | 50% | Wait For DB l... | No | |
| 15 | New Drug Treatm... | 33% | Wait For DB l... | No | |
| 16 | Mgmt of OAB alg... | 0% | Wait For DB l... | No | |
| 17 | ICIQ Modules | 0% | Wait For DB l... | No | |
| 18 | Male Bladder Con... | 0% | Finished | No | Paper does not apply. |
| 19 | Male Bladder Con... | 0% | Finished | No | Paper does not apply. |
| 20 | POP Q | 0% | Wait For DB l... | No | |
| 21 | Sacral Nerve Mod... | 0% | Wait For DB l... | No | |
| 22 | SNM treatment fo... | 66% | Wait For DB l... | No | |
| 23 | Sling with vaginal... | 50% | Wait For DB l... | No | |

```
<Agent Name="Disposable for Stress Incontinence treatment">
    <Switch SwitchCaption="Patient Age:">
        <Case Input="0" Caption="age greater than or equal 19 years">
            <Switch SwitchCaption="Patient Gender">
                <Case Input="0" Caption="Male">
                    <Output>Output for Case 0 Use Anal probe PRB055</Output>
                </Case>
                <Case Input="1" Caption="Female">
                    <Output>Output for Case 1 Use Vaginal probe PRB450</Output>
                </Case>
            </Switch>
        </Case>
        <Case Input="1" Caption="age less than 19 years">
            <Output>Output for Case 1 Use patches ELE428</Output>
        </Case>
    </Switch>
</Agent>
```

FIG. 14A

```xml
<?xml version="1.0" encoding="utf-8"?>
<Agent Name = "ALPP" QuestionnaireID ="61" AgentQID="" AgentID="2" Version ="1.00">
  <IDAliases  AliasList =
        " @QstIsUrgeRuledOut = 606
        ; @QstALPPreadingRange=607
        ; @QstMUCPreading=608
        ; @QstDoBladderNeckRemainClosed = 609
        ; @QstUrethralHypermobility = 610
        ; @QstALPPgt100SuggestsType1or2 = 611
        ; @QstALPPlt60SuggestsType3 = 612
        ; @QstMUCPlt20cmH2OsuggestsType3 = 613
        ; @QstType1StressIncontinence=614
        ; @QstType2StressIncontinence=615
        ; @QstType3SIIntrinsicSD = 616
        ; @QstUrgencyIsNotRuledOut = 617
        ; @QstMUCPge20cmH2O = 594
        ; @QstALPPlt100andgt60 = 595
        ; @QstIsMUCPlt20cmH2O = 596
        ;
        ; @ChoYes = 53
        ; @ChoNo = 54
        ; @ChoAngleOfTheBladderNeckShifts = 879
        ; @ChoBladderNeckIsOpenDuringFilling_MUCPisLow = 880
        ;
        ; @QryTypePatInfo@ = 1
        ; @QryTypeGetAnswer@ = 2
        ; @QryTypeGetTestInfo@ = 3
        ; @QryCustom@ = 4
        ; @Agent3QnrID@ = 61
        ">
  </IDAliases>
  <Switch SwNum ="1"  QID = "@QstIsUrgeRuledOut" SwitchCaption="Is Urge Ruled Out" InputType="iList">
      <iListFilter
          QueryType = "@QryTypeGetAnswer@"
          QstID ="@QstIsUrgeRuledOut"
          QnrID ="@Agent3QnrID@"
          OutputFilter= "0:[ChoiceIndex] = 1; 1:[ChoiceIndex] = 2"
          FieldNames = "ChoiceIndex,ChoiceText"
      > </iListFilter>
      <Case Input= "1"  CID ="@ChoNo"  CaseCaption ="No Urgency Is Not Ruled Out" SwNum ="2" >
        <Output QID = "@QstUrgencyIsNotRuledOut" SwNum ="3"> Urgency is not ruled out.Agent is not applied.</Output>
      </Case>
      <Case Input= "0"  CID ="@ChoYes" CaseCaption ="Yes Urgency Is Ruled Out" SwNum ="4">
        <Switch SwNum ="5"  QID = "@QstALPPreadingRange" SwitchCaption="ALPP reading Range" InputType="iList">
          <iListFilter
              QueryType = "@QryTypeGetAnswer@"
              QstID ="@QstALPPreadingRange"
              QnrID ="@Agent3QnrID@"
              OutputFilter= "0:[TextAnswer] >100; 1:[TextAnswer] <60; 2:[TextAnswer] >=60 AND [TextAnswer] <=100"
              FieldNames = "TextAnswer"
          > </iListFilter>
          <Case Input= "0"  QID = "@QstALPPgt100SuggestsType1or2" CaseCaption ="ALPP gt 100 Suggests Type 1 or 2" SwNum ="6" >
            <Output QID = "@QstALPPgt100SuggestsType1or2" SwNum ="7"> Suggests Type 1 or 2</Output>
          </Case>
```

```xml
        <Case Input= "1"  QID = "@QstALPPlt60SuggestsType3"   CaseCaption ="ALPP lt 60 Suggests Type 3" SwNum ="8" >
            <Output QID = "@QstALPPlt60SuggestsType3" SwNum ="9">Suggests Type 3</Output>
        </Case>
        <Case Input= "2"  QID = "@QstALPPlt100andgt60"   CaseCaption ="ALPP between 60 and 100" SwNum ="10" >
            <Switch SwNum ="11" QID = "@QstMUCPreading" SwitchCaption="Is MUCP reading less 20 " InputType="iList">
                <iListFilter
                  QueryType = "@QryTypeGetAnswer@"
                  QstID ="@QstMUCPreading"
                  QnrID ="@Agent3QnrID@"
                  FieldNames = "TextAnswer"
                  OutputFilter= "0:[TextAnswer] <20; 1:[TextAnswer] >=20"
                > </iListFilter>
                <Case Input= "0"  QID = "@QstMUCPlt20cmH2OsuggestsType3"   CaseCaption ="MUCP less then 20 cmH2O" SwNum ="12" >
                    <Output QID = "@QstMUCPlt20cmH2OsuggestsType3" SwNum ="13">MUCP lt 20 cmH2Osuggests Type 3</Output>
                </Case>
                <Case Input= "1"  QID = "@QstMUCPge20cmH2O"   CaseCaption ="MUCP ge 20cmH2O" SwNum ="14" >
                    <Switch SwNum ="15" QID = "@QstDoBladderNeckRemainClosed" SwitchCaption="Do Bladder Neck and Urethra remain closed?" InputType="iList">
                        <iListFilter
                          QueryType = "@QryTypeGetAnswer@"
                          QstID ="@QstDoBladderNeckRemainClosed"
                          QnrID ="@Agent3QnrID@"
                          FieldNames = "ChoiceIndex,ChoiceText"
                          OutputFilter= "0:[ChoiceIndex] = 1; 1:[ChoiceIndex] = 2"
                        > </iListFilter>
                        <Case Input= "0"  CID ="@ChoYes"  CaseCaption ="Yes" SwNum ="16" >
                            <Output QID = "@QstType1StressIncontinence" SwNum ="17">Type 1 Stress Incontinence</Output>
                        </Case>
                        <Case Input= "1"  CID ="@ChoNo"  CaseCaption ="No" SwNum ="18" >
                            <Switch SwNum ="19" QID = "@QstUrethralHypermobility" SwitchCaption="Urethral Hypermobility" InputType="iList">
                                <iListFilter
                                  QueryType = "@QryTypeGetAnswer@"
                                  QstID ="@QstUrethralHypermobility"
                                  QnrID ="@Agent3QnrID@"
                                  FieldNames = "ChoiceIndex,ChoiceText"
                                  OutputFilter= "0:[ChoiceIndex] = 1; 1:[ChoiceIndex] = 2"
                                > </iListFilter>
                                <Case Input= "0"  CID ="@ChoAngleOfTheBladderNeckShifts"  CaseCaption ="Angle of the bladder neck shifts" SwNum ="20" >
                                    <Output QID = "@QstType2StressIncontinence" SwNum ="21">Type 2 Stress Incontinence</Output>
                                </Case>
                                <Case Input= "1"  CID ="@ChoBladderNeckIsOpenDuringFilling_MUCPisLow" CaseCaption ="Bladder Neck is open DURING filling - MUCP is low" SwNum ="22" >
                                    <Output QID = "@QstType3SIIntrinsicSD" SwNum ="23">Type 3 Stress Incontinence - Intrinsic Sphincteric Defficiency</Output>
                                </Case>
                            </Switch>
                        </Case>
                    </Switch>
                </Case>
            </Switch>
        </Case>
    </Switch>
</Case>
        </Switch>
    </Case>
</Switch>
</Agent>
```

US 8,447,783 B2

INTELLIGENT AGENT AND MANAGER SYSTEM

This patent application claims the benefit of U.S. Provisional Patent Application No. 61/349,557, filed May 28, 2010, which is hereby incorporated by reference.

I. FIELD OF THE INVENTION

This invention relates to an expert system having one or more agents working in parallel to provide recommendations based on information provided by an agent manager and/or at least one database.

II. BACKGROUND OF THE INVENTION

Previous expert systems (particularly in medicine) have been used to supply the user with online/automated facility where a diagnostic determination is aided by a monolithic and sophisticated algorithm using expert rules and inference engines. What makes these "all encompassing" expert systems unmanageable relates to the difficulty in validating and updating new rules within the framework of a large expert system.

In the practice of medicine, all the references that clinicians use to help make their diagnosis and treatment plans must be validated. Large expert systems are difficult to design for any utility for the physician due to the inverse relationship between complexity of algorithms and testability. In order for expert systems to properly assist its human user, there must be a large degree of completeness/thoroughness. However, making sure all the rules embedded in such software are accurate would be a large undertaking particularly when you begin to add and modify new rules over time as there are developments in the field. An expert system is only useful if the algorithms contained in such a system are current (embedding the latest and more relevant information available).

III. SUMMARY OF THE INVENTION

In any field requiring expertise (e.g., medicine, law, mechanical diagnostics, even science studies), the ability to remember important information at the appropriate time is always important (if not critical). The internet and computer search engines have done a remarkable job in organizing the data for practical use. However, when one practices in an expert field (e.g., medicine, law, service repairs, diagnostics of any kind), the user is either in "expert mode" where their personal recollection of information is based on his/her own ability to remember this information or the user goes into "research mode" where they consult information databases to look for relevant precedent information. "Research mode" could be any activity such as searching on the internet, reviewing past scientific journals, calling an expert colleague, and so on.

The agent system in at least one embodiment includes an interactive solution to monitor relevant inputs and provide timely and appropriate outputs based on current scientific data which aid the user to make an informed decision. Rather than worry about creating one large software/flowchart system, the agent system in at least one embodiment includes a plurality of agents and an agent manager.

Using electronic search tools and reading all the papers is the traditional way of arriving at an informed decision. However since this effort is very time-consuming, many experts do not rely on this method—opting instead to use their experience to handle more of the routine situations. However, the agent system in at least one embodiment will allow the user to always have substantially up-to-date information about any new changing field of expertise that they subscribe to—much like subscribing to a scientific journal which sends out regular periodicals but without the need to have to read and recall all that information. In at least one embodiment, the source for the information used to create the agent is provided to the professional using the system. Nothing in this disclosure should be interpreted as replacing the judgment of the professional using a system built according to this invention. The invention in at least one embodiment is intended to augment the information available to the professional to assist the professional in his/her decision-making process.

In at least one embodiment, the agent manager keeps all agents running concurrently—giving the user an overview dashboard of all the running agents and their running status. Some agents are dormant, waiting for input, some are processing data and waiting for more data, and others are finished based on receiving and processing all the inputs they require.

In a further embodiment, the agents work with the agent manager to report the running status of the agent (stopped, waiting, in process, completed). Each agent works independently from all the other agents (unless one agent relies on the output of another agent).

In at least one embodiment, the agents are separated from the agent manager to allow the inclusion and modification of new agents possible without disturbing the existing agents. Also, in at least one embodiment each agent is supported by reference literature (or other material) allowing the validation of the algorithms to be manageable and easy to verify.

In at least one embodiment, each agent is meta-tagged and can be organized by subject matter, possibly connected or linked appropriately or searchable. The tracking of agent activity and use will allow for audit trails and individual usage monitoring to occur.

In at least one embodiment, the agent is a representation of one single scientific publication. A typical scientific publication usually consists of a basic algorithm or analysis that has been proposed, constructed, tested, analyzed and cleared for publication in a recognized scientific journal. The papers are typically reviewed by expert peers and cleared for publication. The papers themselves remain static records of these experiments. It is assumed the reader (clinician) will remember this information for useful application to a new relevant situation (i.e., a new patient exhibiting the same conditions or a client with the same legal situation). The agent in at least one embodiment includes a distillation of the scientific paper that runs in the background of any database (e.g., electronic medical record system containing clinical decision support data points) ready to provide an output if the input conditions are met.

In at least one embodiment, the invention includes a system including: an agent manager having an interface for interacting with at least one external database, an internal database, and a controller connected to the interface and the internal database; and a plurality of agents in communication with the agent manager, each agent having a plurality of flow steps for processing information substantially in parallel with the other agents to provide an output to at least one of the agent manager and an agent database interface for communicating with at least one external database, the output is based on at least one input by the agent; and wherein the internal database of the agent manager includes an entry for each agent in communication with the agent manager. In a further embodiment, each entry in the internal database includes a technical area for each agent, and the controller controls the flow of information from the interface to the plurality of agents based at least on the technical area of each agent in the internal database. In a further embodiment, the controller publishes all information received through the interface to all agents in communication with the agent manager. In a further embodiment, the controller includes a display generator, the display generator creates a graphical user interface for displaying any output received from agents in communication with the agent manager. In a further embodiment, the controller monitors the operation of the agents and displays this information. In a further embodiment, the interface monitors the availability of data in any database in communication with the interface, and in at least one embodiment the controller publishes data as it becomes available in any database. In a further embodiment, the interface monitors any database in communication with the interface for predetermined events before pulling data for publication by the controller to any agents in communication with the agent manager.

In at least one embodiment, the invention includes a method for providing assistance to a professional based on at least part of available material in the professional's field, the method including: receiving information with an agent manager from an expert system, the received information is to be analyzed by a plurality of agents; distributing the information to the agents in communication with the agent manager; monitoring and displaying the progress of the agents with the agent manager; and receiving and reporting to at least one of a database and a human user any results provided by the agents to the agent manager. In a further embodiment, the information is distributed to agents based on the information received. In a further embodiment, the method further includes maintaining an internal database in the agent manager having an entry for each agent in communication with the agent manager; and updating the internal database when there is a change in the agents in communication with the agent manager. In at least one embodiment, distributing the information is based on entries in the internal database that includes, for example, a technical area for each agent in communication with the agent manager. In a further embodiment, the method further includes tracking the inputs for each agent in communication with the agent manager; and assembling a questionnaire for use by the professional that includes questions to gather the inputs for the agents. In a still further embodiment, the method further includes maintaining a patient-agent database with each entry identifying a link created between each patient and each agent that patient information had been exchanged about.

In at least one embodiment, the invention includes a method including: capturing a plurality of data with a data capture module; populating a database with the captured data; performing at least one of monitoring the database for the addition of data and notifying with the data capture module an agent manager when the data capture is done; notifying agents by the agent manager to retrieve data; retrieving data from the database by the agents; and outputting information from each agent that retrieved data to at least one of the agent manager and the database.

Given the following enabling description of the drawings, the invention should become evident to a person of ordinary skill in the art.

IV. BRIEF DESCRIPTION OF THE DRAWINGS

FIG. 4 illustrates an example interface for use in at least one embodiment of the invention.

FIGS. 7A and 7B illustrate additional example interfaces for use in at least one embodiment of the invention.

FIGS. 13A-13C illustrate different interfaces for use with at least one embodiment of the invention.

FIGS. 14A and 14B illustrate examples of different agents according to an embodiment of the invention.

V. DETAILED DESCRIPTION OF THE DRAWINGS

FIGS. 1-19 illustrate different aspects of different embodiments according to the invention.

Figure 1:
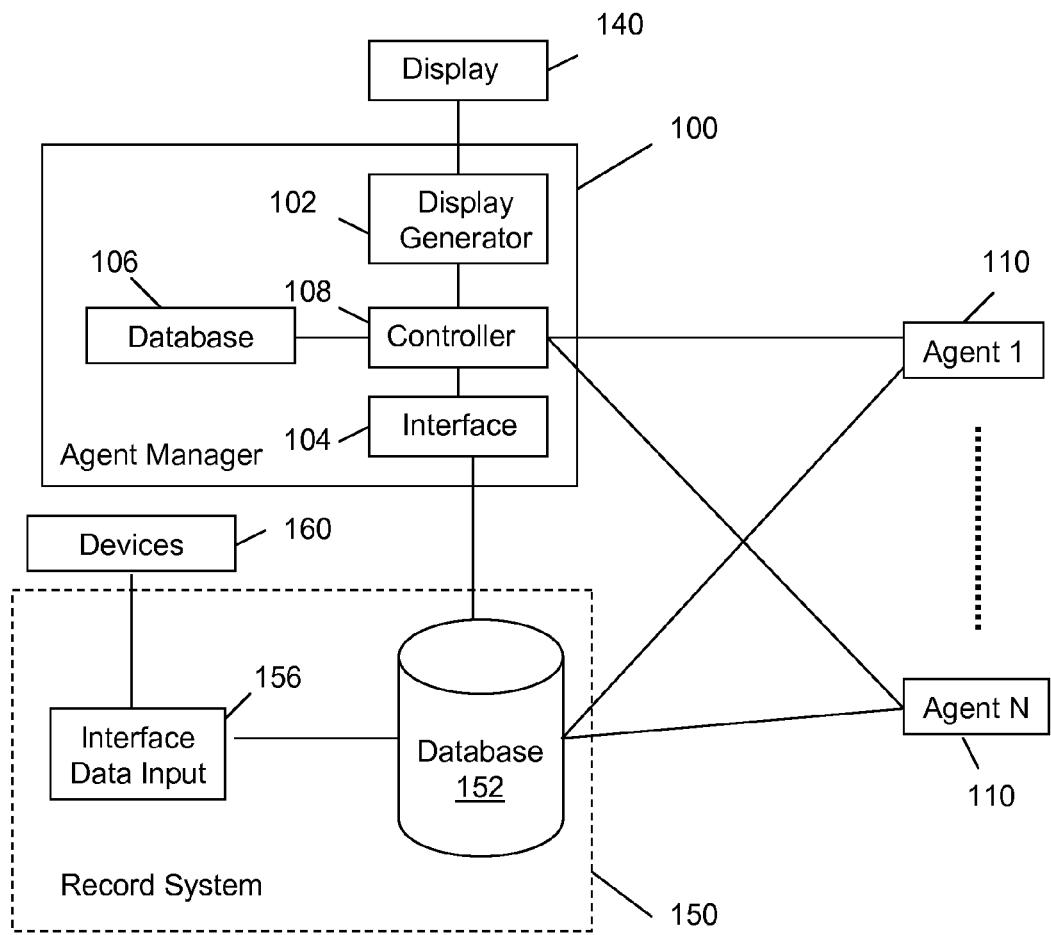
FIG. 1 illustrates a block diagram according to an embodiment of the invention.

FIG. 1 illustrates an embodiment according to the invention that includes an agent manager 100 in communication with a plurality of agents 110 that operate substantially in parallel to each other. In the various described embodiments, the agent manager 100 and the agents 110 are in communication with a record system 150 that provides patient information for processing by the agents 110. In at least one embodiment, the record system 150 includes at least one database 152 having a variety of data fields that are associated with one or more agents 110 where the fields can be populated based on, for example, data provided by other devices 160, responses received to queries by the record system 150 to the user or manual entry by the user through an interface 156. In a further embodiment, the record system 150 is replaced by a data intake module that, for example, receives information from the user or pulls the needed information from other sources including databases, public records, court records, etc. In an alternative embodiment, the agent manager 110 receives the data and any other information from user without the presence of the record system 150.

FIG. 1 illustrates an example of an agent manager 100 including a display generator 102, an interface 104, an internal database (or agent database) 106, and a controller 108. The interface 104 provides the connection between the controller 108 and the external database 152 or other software package that provides a notification of when data is ready in the database 152 for analysis. The internal database 106 in at least one embodiment includes an entry for each agent 110 in communication with the agent manager 100 and in further embodiments includes a technical area for each of those agents 110. The controller 108 is in communication with the internal database 106 and the plurality of agents 110 to act as a conduit of information in at least one embodiment between the database 152 and the agents 110. Based on this disclosure, it should be appreciated that the agent manager 100 may take a variety of forms as discussed in this disclosure. In an alternative embodiment, the database 106 is omitted.

The agents 110 communicate with the agent manager 100 and in at least one embodiment the agents 110 also communicate directly or indirectly with at least one database 152 housing information that serves as one or more inputs into the agents 110. In at least one embodiment, the agent manager 100 provides status information regarding each agent 110 running and in further embodiments the status information is also provided based on a record identifier that provides a status or an output that in at least one embodiment includes a recommendation as to further action or non-action.

FIG. 1 illustrates one example embodiment according to the invention. The illustrated embodiment includes an agent manager 100 in communication with a plurality of agents 110 as represented by Agent 1 . . . Agent N. As used in this disclosure "in communication" includes physical and wireless connections that are indirect through one or more additional components (or over a network) or directly between the two components described as being in communication. In at least one embodiment, the agent manager 100 and agents 110 operate on one computer with at least one processor running software providing the functionality of the agent manager and the agents and as such is a computer having a processor running specific code.

FIG. 1 illustrates additional components that provide context for the system, but in at least one embodiment the additional components are part of the overall system. At least one external (or source) database 152 can be in communication with the agent manager 100 and the plurality of agents 110. The database 152 provides data to be analyzed by the agents 110. Also illustrated is a data input 156 that may take a variety of forms including a user interface running on a computing device, a data interface to another database, or a data interface to medical equipment or other measurement equipment. The computing device includes a computer or other processing device having a processor running software. The data input and the database together are examples of components that are found in many electronic medical record systems. The agent manger 100 may provide a variety of outputs including, for example, a display, a printer, a computer readable medium, or network connection for sending the data to another device. In at least one implementation, the agent manager 100 includes a display generator 102 that creates the interface to be shown on any attached or in communication display 140.

Figure 2:
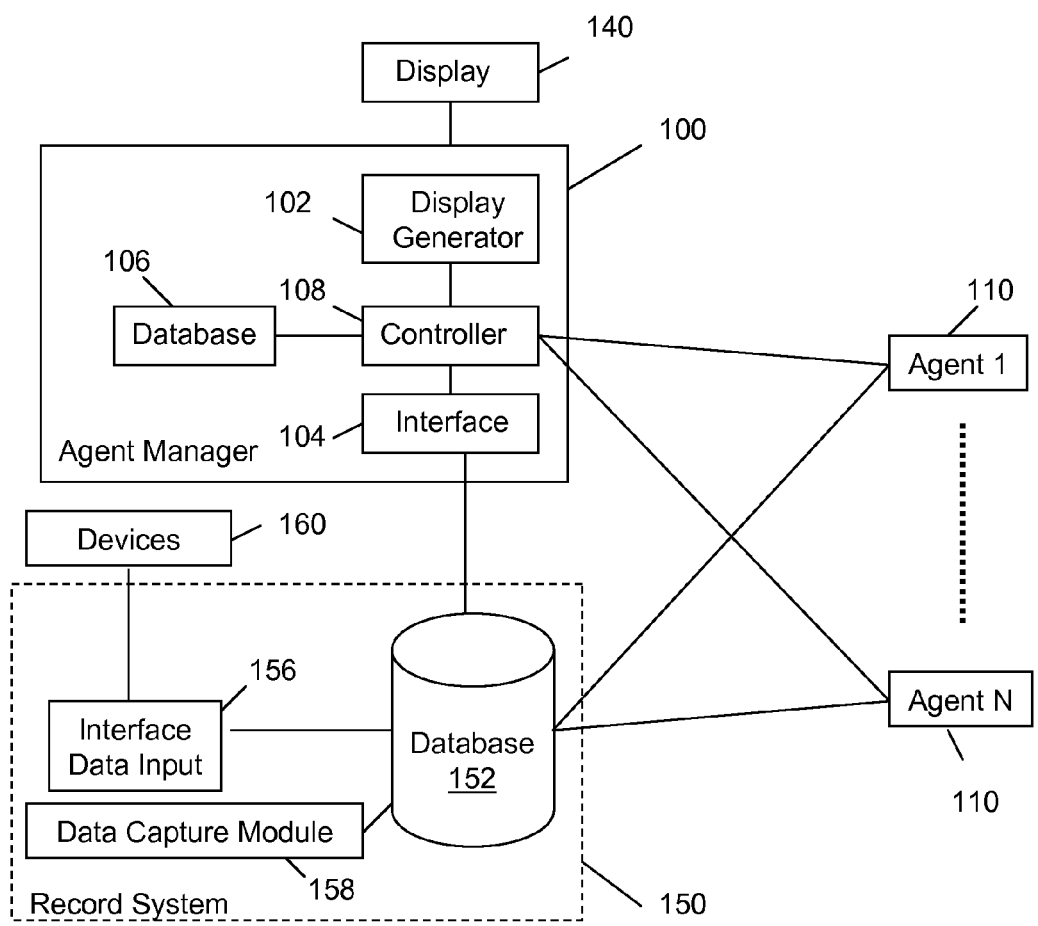
FIG. 2 illustrates a block diagram according to another embodiment of the invention.
Figure 3:
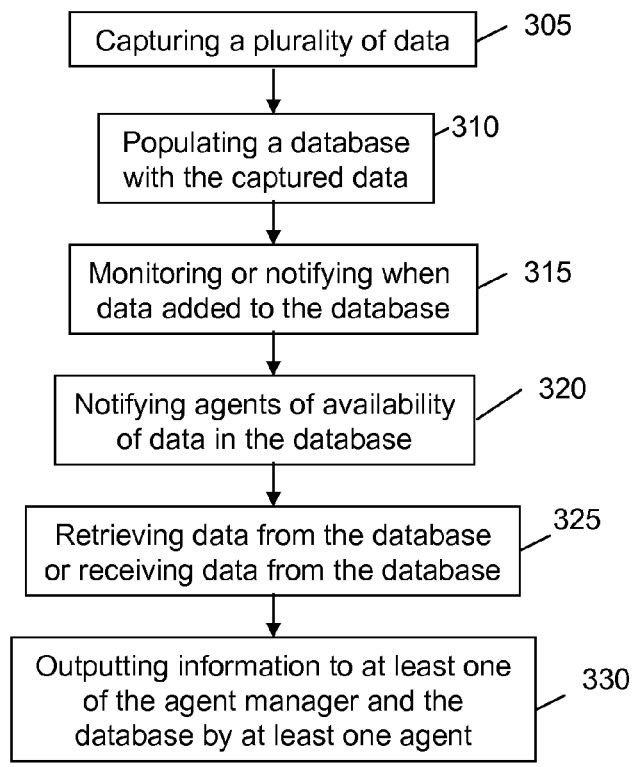
FIG. 3 illustrates a flowchart according to an embodiment of the invention.

FIG. 2 illustrates another example embodiment that includes a data capture module 158 connected to the database 152 with the remaining components similar to those illustrated in FIG. 1. The data capture module 158 in at least one embodiment includes an interface for receiving data and/or information from the user. FIG. 3 illustrates an example method for operation of the system illustrated in FIG. 2. The data capture module 158 in at least one embodiment captures a plurality of data related to various measurements and readings accumulated during a medical exam, 305. The data capture module populates at least one database 152 with the captured data, 310. The agent manager 100 monitors the database 152 for data activity or alternatively the data capture module 158 signals the agent manager 100 when data is added to the database 152, 315. The agent manager 100 notifies the agents 110 of the availability of data in the database to be analyzed and identifies at least one patient whose data is to be analyzed, 320. Each agent 110 retrieves data from the database 152 based on the data that agent 110 needs to provide an output to the agent manager 100, 325. Alternatively, the agent manager 100 publishes the relevant data to one or more of the agents 110. The agents 110 process the retrieved data and provide an output to the agent manger 100 where the output is a conclusion or an indication of additional data needed, 330.

FIG. 4 illustrates an example of an interface that may be produced by the display generator 102. The recommendation, for example, includes at least one of an additional test, suggestion of one or more medical conditions as a possibility for the patient, and a course of treatment. The indication of additional data needed, for example, includes at least one of a status progression as illustrated in FIG. 4, a textual statement such as waiting for database input or finished, or identification of the data that is required to perform the analysis. In a further embodiment, the agent manager 100 or the agents 110 also provide their results to the data capture module 158, the database 152, and/or a report module. The report module will use the recommendations provided by one or more of the agents along with additional data pulled from the database to populate a report for use by the user.

FIG. 4 also illustrates an example of how the use of color, italics or other indications can be used to relay information as to the status of the respective agent. For example, if the agent has received its necessary inputs and determined that it is not applicable, then it could be displayed in italics with an output indicating that it is not applicable to the current situation. See, e.g., "Femal SUI MUS . . . " (agent 4). If the agent may apply or does apply to the situation, the agent could be written in a regular type with color being used as an indication of status such as blue for awaiting at least one input and green for completed. See, e.g., "Incontinence and . . . " (agent 12). Other color schemes and font styles could be used than those illustrated in FIG. 4 including the use of bold or a particular color to indicate a recommendation of a further test or the possible existence of a particular condition. FIG. 4 also illustrates the use of providing a percentage to indicate the level of progression of individual agents. See, e.g., "New Drug Treatment" (agent 15) at 33% and "SNM treatment for" (agent 22) at 66%. FIG. 4 also illustrates an alternative embodiment where the user may designate particular agents as favorites 410. FIG. 4 also illustrates an example embodiment where the user may select a particular heading 415 and have the agents sorted based on that attribute along with identifying the patient 420 whose data is being processed by the agents.

Figure 5:
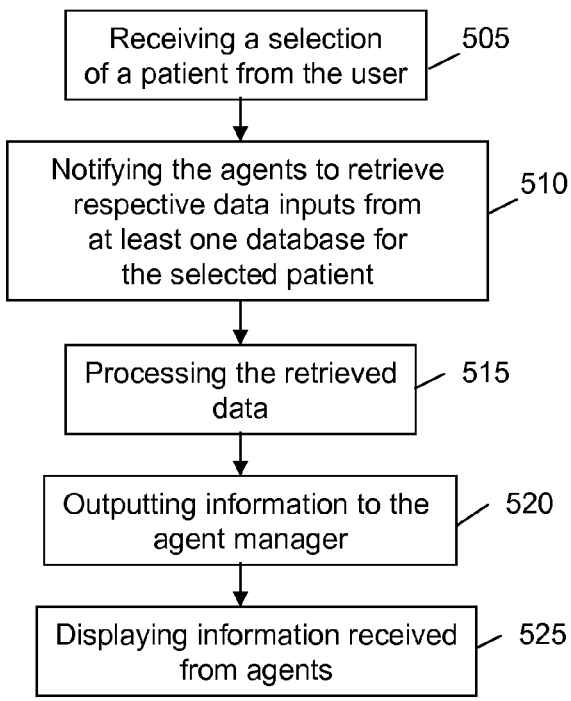
FIG. 5 illustrates a flowchart according to another embodiment of the invention.

FIG. 5 illustrates another example method for operation of the systems illustrated in FIG. 1 or FIG. 2. The use of the agents 110 in the illustrated method is triggered by the user starting the agent manager 100 and selecting a patient to be analyzed, 505. An example of this is illustrated in selection box 420 in FIG. 4. The agent manager 100 in response to the selection of the patient notifies the agents 110 to retrieve their respective data inputs from the database 152 for the identified patient, 510. The agents 110 process the retrieved data, 515, and provide an output to the agent manager 100, 520. FIG. 4 illustrates an example of an interface that can display the status of the agents 110, 525.

In an alternative embodiment to the previous embodiments, the agent manager 100 refers to a database 106 (or table) to determine which data fields are relevant to the attached (or associated) agents. The agent manager 100 pulls the data and publishes it to the agents 110 with all agents receiving the data or there is selective publication based on the contents of the database 106 with the agents receiving the data that is needed as input for the respective agents.

Figure 6:
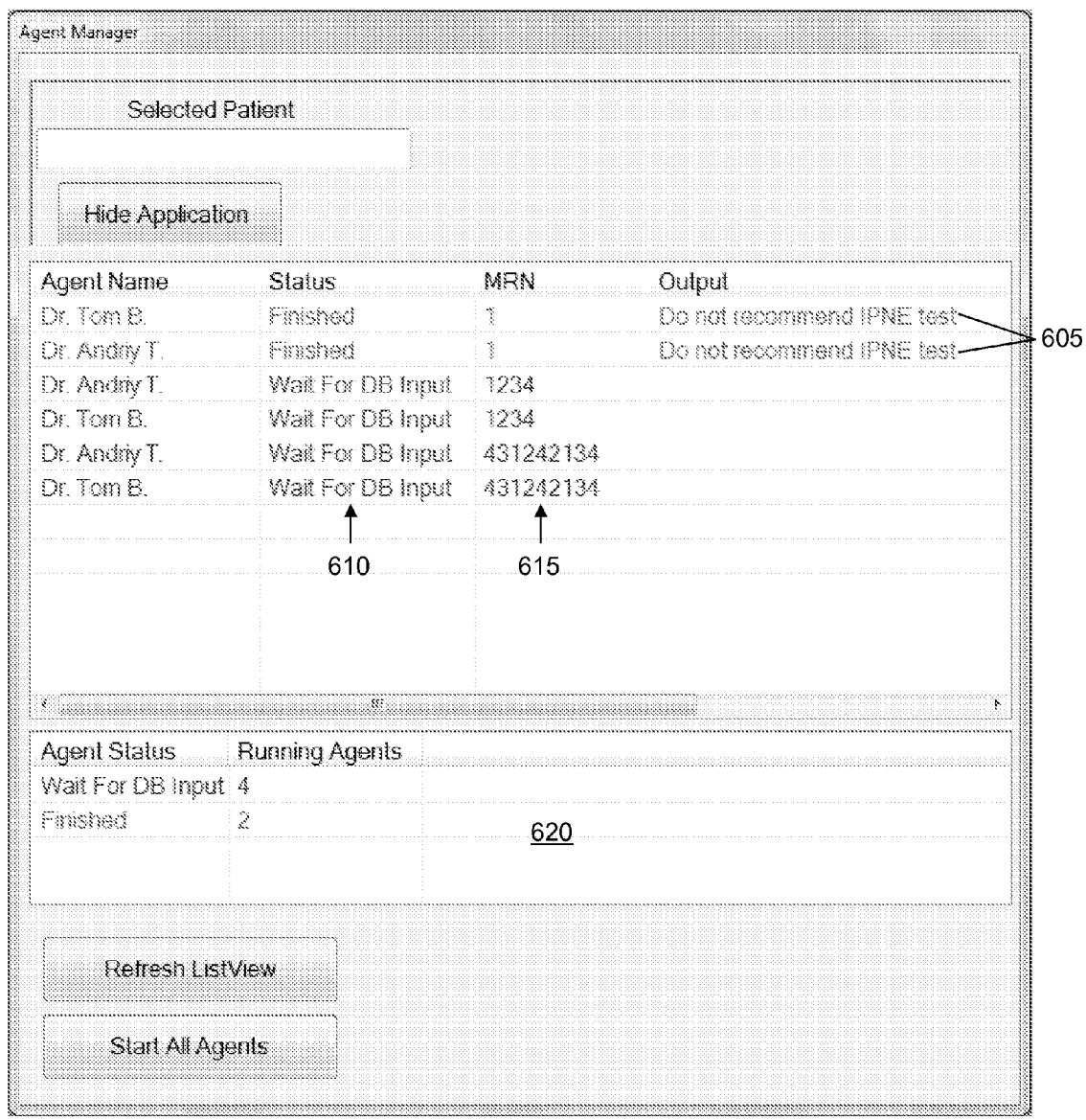
FIG. 6 illustrates another example interface for use in at least one embodiment of the invention.

FIG. 6 illustrates an alternative interface for displaying the status of the agents 110. In this embodiment the agents 110 are running for multiple patients at once. The patients whose information is being analyzed can be selected by the user, be patients being treated that day or other time period, be patients awaiting additional data from, for example, laboratory tests. There are a variety of ways for data needed by the agents 110 to provide their respective outputs moves from the database 152 to the agents 110. One example is for the data to be published to the agents 110. One example of publication includes all data being sent to all of the agents 110 in communication to the database 152 with the agents 110 ignoring the data that is not relevant. Another example of publication is for the database 152 and/or the agent manager 100 to include identification of which agents 110 are interested in which data fields in the database 152 and publish the data only to the interested agents 110 when data in that field changes. In at least one embodiment, the identification of the agents 110 is in a database in the agent manager 100 that serves as the information conduit between the database 152 and the agents 110. The publication may under either example be event driven, for example, once data for a series of fields is complete or a set of questions are answered or a medical examination or other appointment is complete, then the data is published. In at least one embodiment, the publication of data is done via the agent manager 100 receiving the data from the database 152 and forwarding it to one or more of the agents 110.

Another example of how to move data from the database 152 to the agents 110 is having the agents 110 request the data of interest at predetermined time intervals or based on notifications from the agent manager 100 monitoring the database 152 that data is available for requesting (or pulling). In at least one embodiment, the agent manager 100 provides the communication link between the agents 110 and the database 152. To streamline handling of the data, the agent manager 100 may include a cache to retain data for a period of time to decrease the number of transactions with the database 152.

In the illustrated embodiment of FIG. 6, the agents 110 send their respective outputs to the at least one of the agent manager 100 and the database 152. In at least one embodiment, the agent manager 100 displays information to the user through a display generator 102 and a display 140. An example interface for the agent manager 100 is depicted in FIG. 6. The illustrated interface is for a medical environment that is running two agents (Dr. Tom B. and Dr. Andriy T.) and has three medical records (1, 1234, and 431242134) interacting with the agents as represented by three distinct numbers in the MRN column (medical record number). The illustrated interface shows that for MRN 1, the agents have finished processing the data and provided an output of "Do not recommend IPNE test" 605. In connection with the other two medical records, both agents are still waiting to receive at least one input from the database 610. Based on this disclosure, it can be appreciated that other identifiers could be used in place of MRN 615 and still provide a way to correlate the information to, for example, a particular patient, client, project, or database entry using other identifiers including alphanumeric labels or names. FIG. 6 also illustrates an example of a status summary 620 that informs the user the number of agents waiting for an input and the number of agents that are finished.

Figures 7A, 7B:
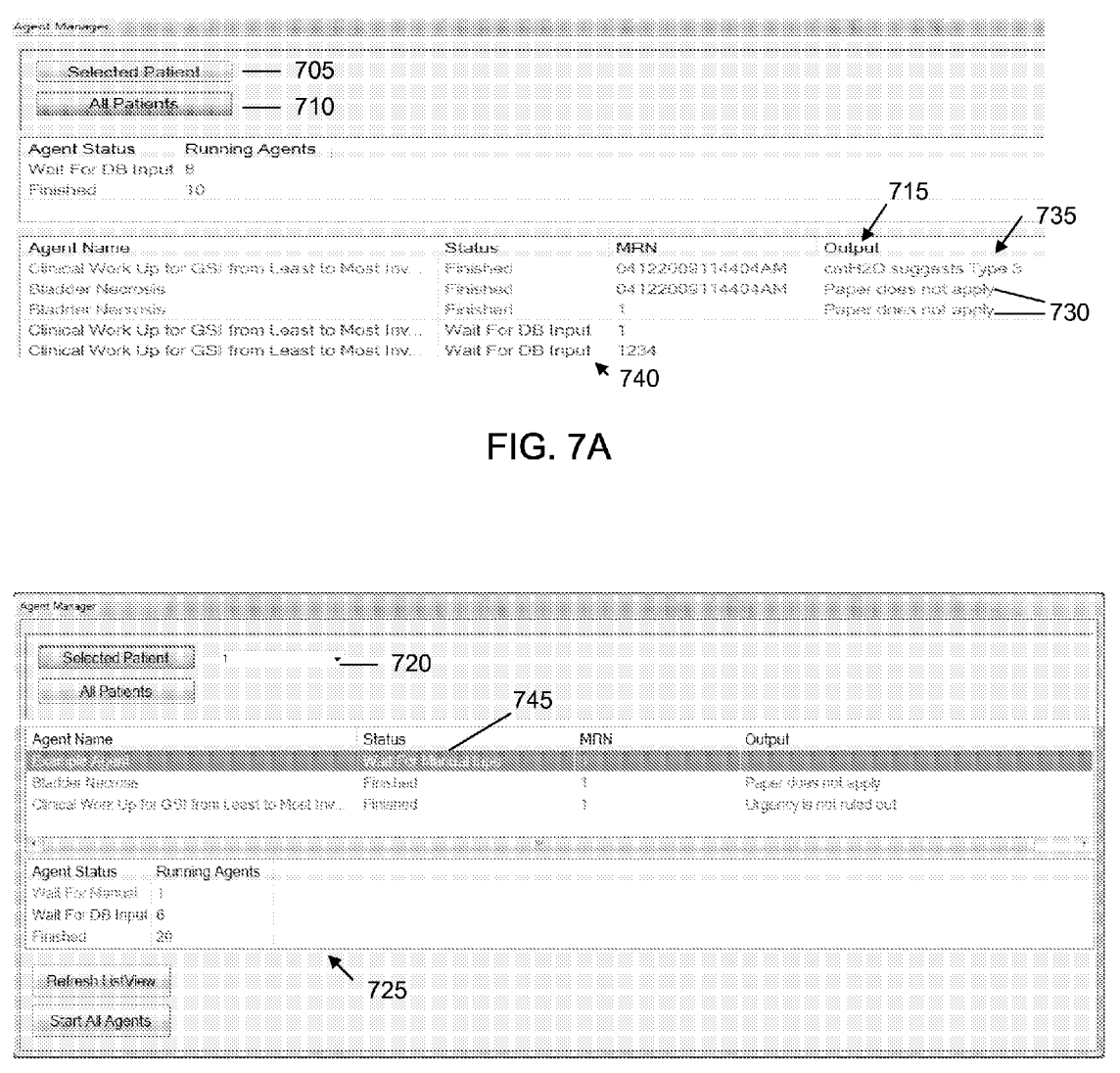

FIGS. 7A and 7B illustrate another example interface for the agent manager 100 in the medical field that includes a "Selected Patient" button 705 and an "All Patients" button 710. FIG. 7A illustrates a partial display of the interface (only 5 Agent Name-MRN combinations are shown even though there are 18 agent-MRN combinations running) that results from the user selecting the "All Patients" button 710. FIG. 7A also illustrates an example where one agent (Bladder Necrosis) is not applicable to two patients 730, because the underlying paper used to create the agent does not apply to those patients' situations as identified by the output 715 of "Paper does not apply" 730. While the "Clinical Work Up . . . " agent is complete with respect to MRN 1 and suggests a recommend condition ("smH2O suggests Type3") 735. While that same agent is awaiting additional information 740 to become available in the database for the other two MRNs identified in FIG. 7A.

FIG. 7B illustrates where the "Selected Patient" button 705 has been selected to allow for selection of a particular patient, which in the illustration is Patient No. 1. Although a pull-down menu 720 is illustrated for selection of the patient, other interfaces could be used such as a text field or a search interface. There are three agent-MRN combinations displayed while there are 27 total agent-MRN combinations being tracked by the Agent Manager. Of the 27 total agent-MRN combinations: 20 are finished, 1 is awaiting manual entry of data, and 6 are awaiting additional data to be provided by the database as indicated in the agent summary section 725. In terms of Patient No. 1, one agent ("Example Agent") is waiting for manual information to be entered 745, for example, through the agent manager or through an interface functionally similar to the one depicted in FIGS. 7A and 7B. The other two agents have their status as "Finished" and as such their respective outputs are displayed in the interface.

Figure 8:
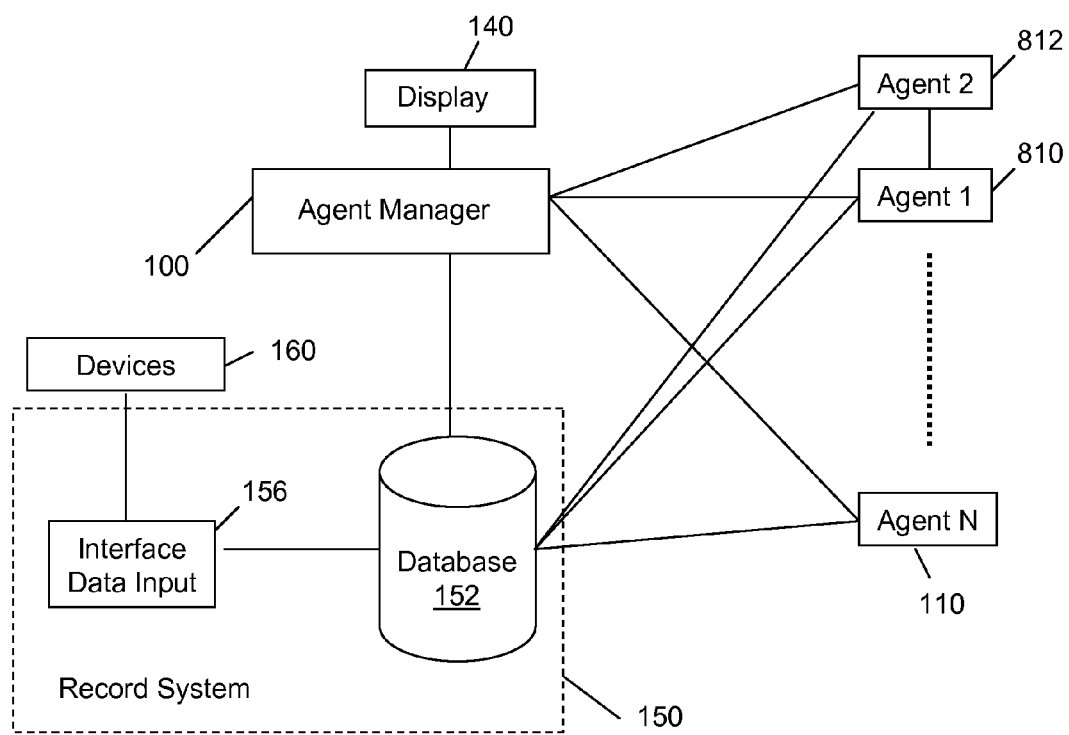
FIG. 8 illustrates a block diagram according to another embodiment of the invention.

FIG. 8 illustrates a further embodiment where a first agent 810 has as an input that is received from an output of another agent (or second agent) 812. In this embodiment, the first agent 810 will monitor the database for receipt of the output of the second agent 812. Alternatively, the first agent 810 will have the agent manager 100 monitor the progress of the second agent 812.

Figure 9:
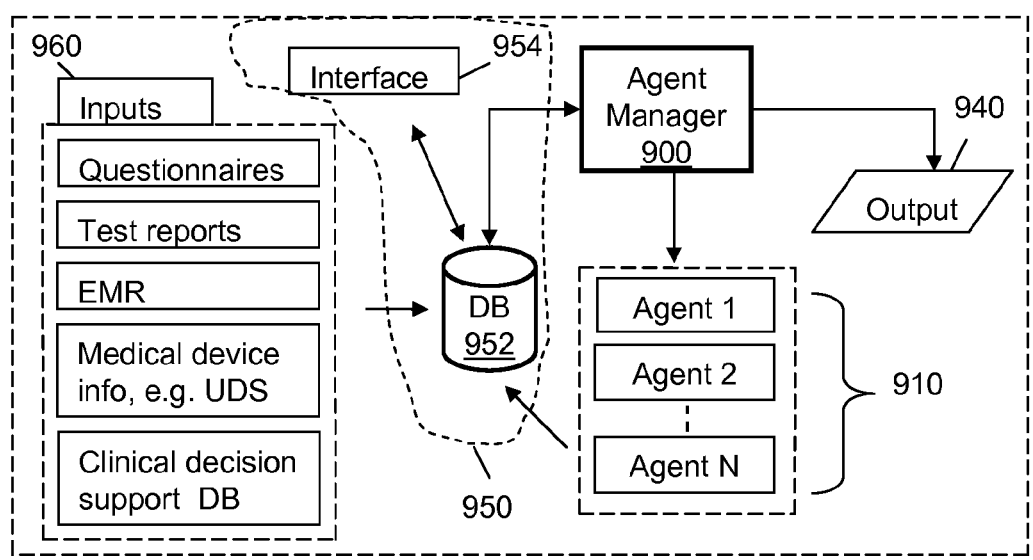
FIG. 9 illustrates a block diagram according to another embodiment of the invention.

FIG. 9 illustrates another example embodiment according to the invention. FIG. 9 illustrates examples of some of the inputs 970 that might be utilized by agents 910 in a medical expert system 950 implementation that includes an interface 954 to interact and receive inputs for the database 952 from the user. Examples of additional inputs for the database 952 from other sources 960 include but are not limited to questionnaires; test or laboratory reports; other electronic medical record systems; medical devices such as pulse oximeters, pressure sensors, and blood pressure cuffs; clinical decision support databases; and identification cards. The data used to populate the database 952 in at least one embodiment is from data entry by the user and/or patient through an interface 954. FIG. 9 illustrates a plurality of inputs 960 and a user interface 954 in communication with a database 952. The database 952 is in communication with an agent manager 900 and a plurality of agents 910. The agent manager 900 in at least one embodiment provides an output as described previously to the user. FIG. 9 also depicts an example of the flow of information between the illustrated components as represented by the various arrowheads.

Figure 10:
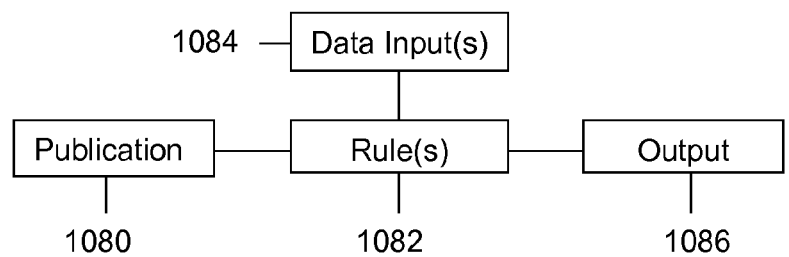
FIG. 10 illustrates a block diagram for an agent according to at least one embodiment of the invention.

FIG. 10 illustrates an example of aspects of each agent including the identification of (or tying to) a publication 1080 that was used to create the rule set 1082 to analyze the data input(s) 1084 to produce an output 1086. The creation of the agents will be discussed in more detail later in the disclosure.

Examples of how the publication 1080 can be associated with a particular agent include a copy of the publication, a citation to the publication, and a link that will take the user to the publication or external source for the publication. The rule set 1082 includes the decision pathways that are followed to provide a recommendation or conclusion that are based on the factors, conclusions, and data contained in the publication (or gathered from experience). Examples of decision pathways are depicted in FIGS. 13A-14B. In at least one embodiment, the different agents are operated using an operation module that uses the rule set 1082 to process the data input(s) 1084 where the operation module is substantially the same for each agent and in a further embodiment the operation module is identical across the agents in the system.

Figure 11:
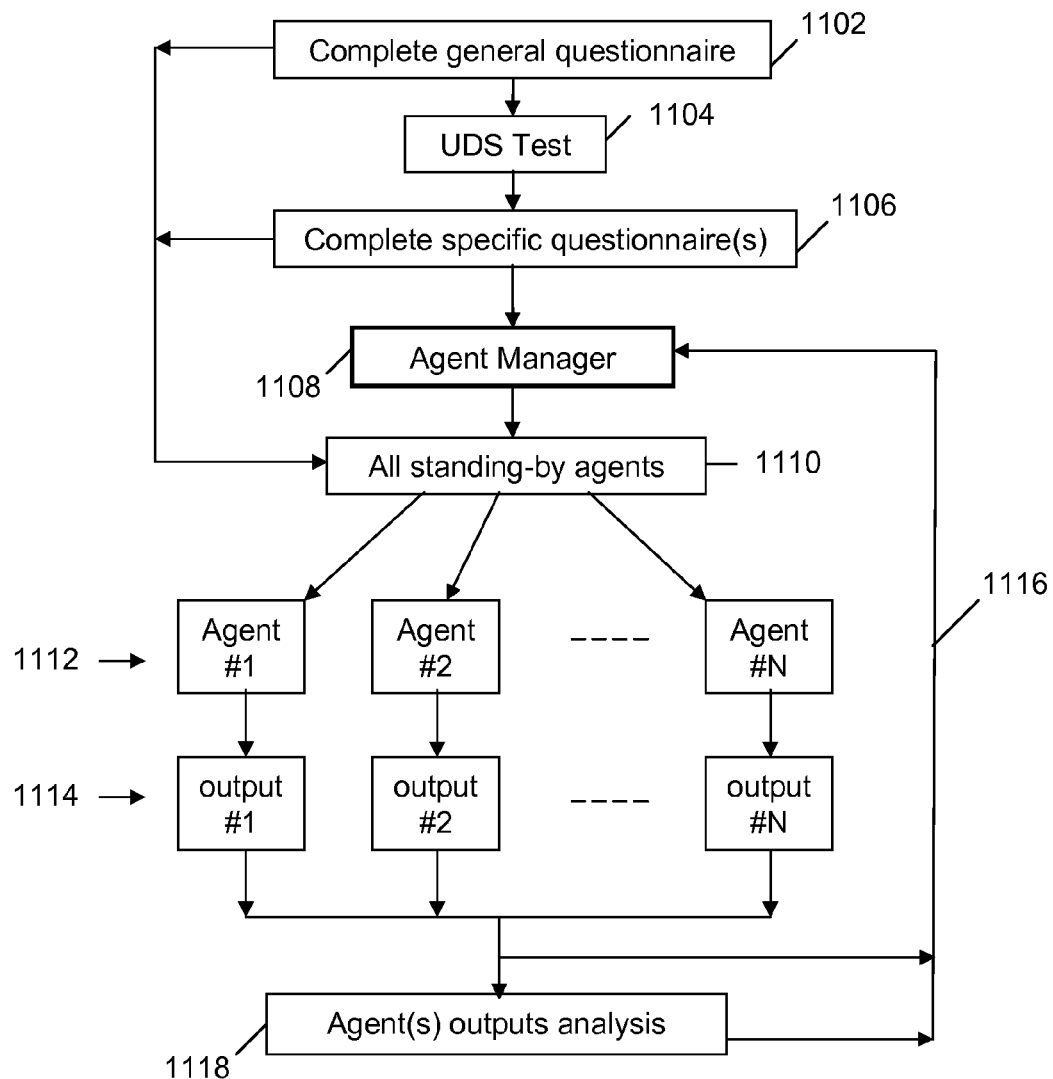
FIG. 11 illustrates a flowchart according to another embodiment of the invention.

FIG. 11 illustrates a method embodiment according to the invention. Although the method illustrates a use of the invention in the medical field, it should be appreciated based on this disclosure that the invention has application in other fields where an expert system would be useful such as legal, mechanical diagnostics, and science studies/research/analysis. The illustrated method includes completion of a general questionnaire such as a medical history 1102, vital sign measurements or tests results 1104, and any health concerns of the patient 1106. This information is received into the database 152. In the illustrated method, an urodynamics test is performed and the results are received into the database, 1104. A more complete and specific questionnaire(s) in at least one embodiment (but this step is omitted in an alternative embodiment) is used to gather additional information for inclusion in the database for the patient, 1106. These three steps could be performed in a different order than illustrated and potentially two or more could be performed concurrently. The illustrated method includes a pair of arrow lines from the questionnaire steps to the all agents standing by step to illustrate that as the data is added to the database, the data in at least one embodiment is published to the agents as illustrated by the arrow lines to Agent #1, #2, and #N, 1110-1114. As mentioned previously, the data instead could be published to the agent manager for distribution to the agents, 1108. The agent manager step illustrates that the agent manager oversees and monitors the progress of the agents as illustrated by the return arrow lines, 1116. As the data flows to the agents, the agents perform analysis according to their rules to provide an output that is then collected by the agent manager and in at least one embodiment is provided to the database, 1118. The method in at least one embodiment allows for the user such as a medical professional to provide a selection that is received by the agent manager as to preferred agent(s) to obtain more details regarding the output of the preferred agent(s). The medical professional then is provided that information to be used in treating the patient from reaching a diagnosis, ordering additional tests, prescribing a course of treatment, etc.

In at least one embodiment, the agent manager includes or is in communication with at least one of an agent table and agent-MRN pair table, which are examples of internal databases on the agent manager. The agent table provides information regarding the different agents that are in communication with the agent manager to facilitate communication with them and to allow for monitoring of the agents. The agent-MRN pair table likewise provides assistance with communication between the agent manager and the agents particularly if one MRN is selected to be able to determine which agents have been associated with the MRN and thus displayed.

Figure 12:
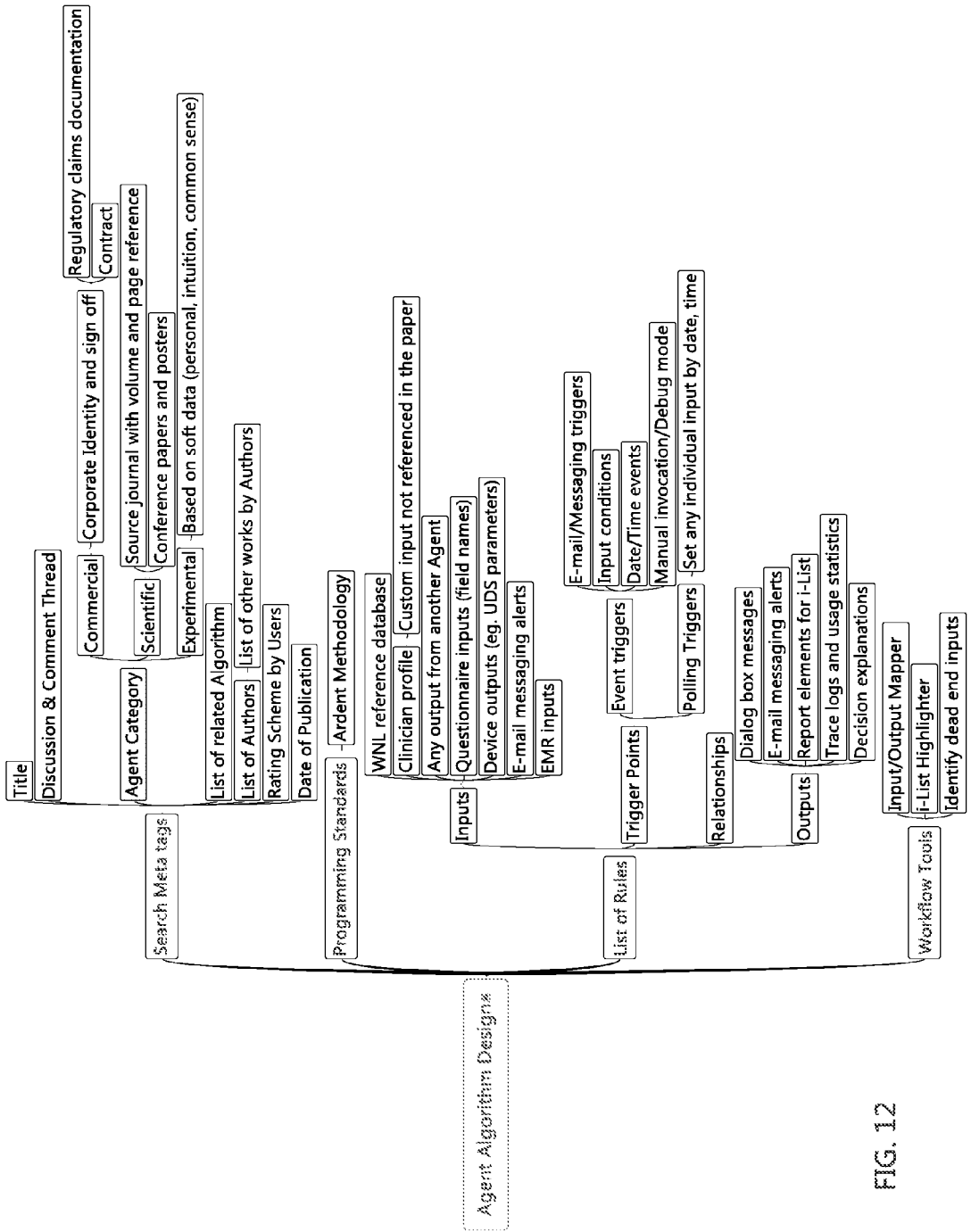
FIG. 12 illustrates an agent algorithm design approach according to an embodiment of the invention.

The agent table in at least one embodiment includes information about each agent and may include further links to additional databases, for example, to pull biographical information about the agent. Examples of the biographical information include list of authors, journal citation, meta tags (FIG. 12 provides some examples) or other searchable file, and title. The list of authors allows individuals to locate agents that are from articles written or other material prepared by particular authors that can assist in locating articles of more interest to the user, because for example they may have trained under a particular expert (or professional in the field like a doctor or lawyer) who is also an author. The meta tags may include identification of other articles or material such as an author of interest, and also in a further embodiment if there are other agents that are based on material from that author. The meta tags in a further embodiment may include rating information gathered from users such as comments and ratings of the agent to assist others in the field in selecting agents that the field finds useful for their practice or conversely that may have issues. The date of publication provides a few benefits including allowing the agents to be sorted based on the date of the information used to create the agent and provide potentially more weight to later agents.

In at least one embodiment, the table will include at least one of an identification of the agent such as an unique identifier (or ID), a path and a name of the agent executable file (for example, if the agent requires a particular custom agent executable to run), name of the agent's .xml file (or other source file) with examples of the source file illustrated in FIGS. 14A and 14B, the type of agent, whether the agent is enabled, and whether there is a popup output for warning. If the path and file name or .xml file information is blank, then the agent manager can use the default location and the name of the agent to locate these files. In another embodiment, if there is no identification of an agent executable file, then the default agent executable file is used.

The agent type in at least one embodiment includes at least one of the following: a poll status, a trigger status, or a patient status. The poll status provides for the agent to be activated by the agent manager according to a predetermined schedule (e.g., hourly during the business day, hourly, daily, each business day, weekly, bi-weekly, monthly, etc.) and run for all of the patients in the database. In a further embodiment, when an agent is set to poll status, the agent is run for patients in the database that have had an information change since the last running or if a new agent against a selection of patients (e.g., all patients, all active patients, patients seen recently or in the last year). The trigger status causes the agent to be activated for example by a trigger (e.g., SQL trigger) that causes the agent to run when a particular field in the database that has a change in the data field. The patient status provides for the agent to be activated if the user selects a particular patient in the agent manager.

The enabled and popup output fields allow the agent manager to know whether the agent is available for launch and whether the agent includes the ability to inform the medical professional of a potential dangerous condition of the patient during execution of the agent for a particular patient.

FIG. 12 illustrates an example of the agent algorithm design. The agents can be based on a variety of sources including, for example, commercial literature, regulating claims documentation, scientific, and experience of an individual(s). The scientific source would find its basis in, for example, a source journal article(s), conference material such as a paper or poster presentation, or a combination of these. The experience category in at least one embodiment includes agents created based on approaches taken by individuals in the field including experts, recognized leaders, or people in the field. The agents may be created for use of a select group of people or distributed to a wider audience. Examples of a category that might be used in the legal field include court opinions, statutes, agreements, treaties, administrative rules, and memorandums.

FIG. 12 identifies examples of workflow tools that include an input/output mapper, identification of important inputs, and identification of dead end inputs. In at least one embodiment, the input/output mapper is included to provide links between the inputs needed for an agent and the outputs that will be produced by the agent with linkage of how the inputs relate to the outputs. As discussed previously, one example of the input/output mapper is a database or table resident in the agent manager. The identification of important inputs allows the agent manager to control the flow of information and in at least one embodiment the activation of particular agents. An example is if an agent needs one particular input, then it will not be activated until that input is available with one way to do that is with the trigger status discussed previously. This feature can also be used to provide a confidence level for the output being provided by the agent that would improve as additional information is provided as inputs to the agent. The identity of dead end inputs allows the agent manager to ignore certain data that is not relevant to the agents with an example of data being the name of the person, which typically would not have any impact on the medical condition of a patient unless that information was used to build a family medical history to use to diagnosis the patient.

FIG. 12 illustrates examples of rules that may govern the operation of the agents from inputs, trigger points, relationships, and outputs. For a particular agent, some of the example rules may or may not be applicable depending on the structure of that agent.

Examples of inputs for any agent include WNL (within normal limits) reference database, clinician profile such as a custom input not referenced in the source material like a paper, an output from another agent, questionnaire inputs from a questionnaire that includes questions to obtain information of relevance for the agent or identification of fields in a database, device outputs such as UDS parameters or a vital signs monitor, e-mail messaging or other forms of messaging, and electronic medical records (EMR) inputs. The questionnaire could include questions that provide information useful for multiple agents.

In at least one embodiment, the agent manager tracks questionnaire inputs for all of the enable agents to accumulate them into a questionnaire for the professional to go through as part of the process such as a patient visit. In a further embodiment, the agent manager provides the electronic medical record system with the questionnaire(s) or the interface(s) to gather the information for the agents in communication with the agent manager. In a further embodiment where the agent manager includes a database, when an agent is added to the system, an entry is made in the database to correlate its input(s) with existing questions in a questionnaire or fields in a database so that the data provided can be appropriately sent to the agent. When the agent requires an input that does not exist, then in at least one embodiment the questionnaire is modified to include a question directed at obtaining information for the input(s) needed by the agent.

Figures 13A, 13B:
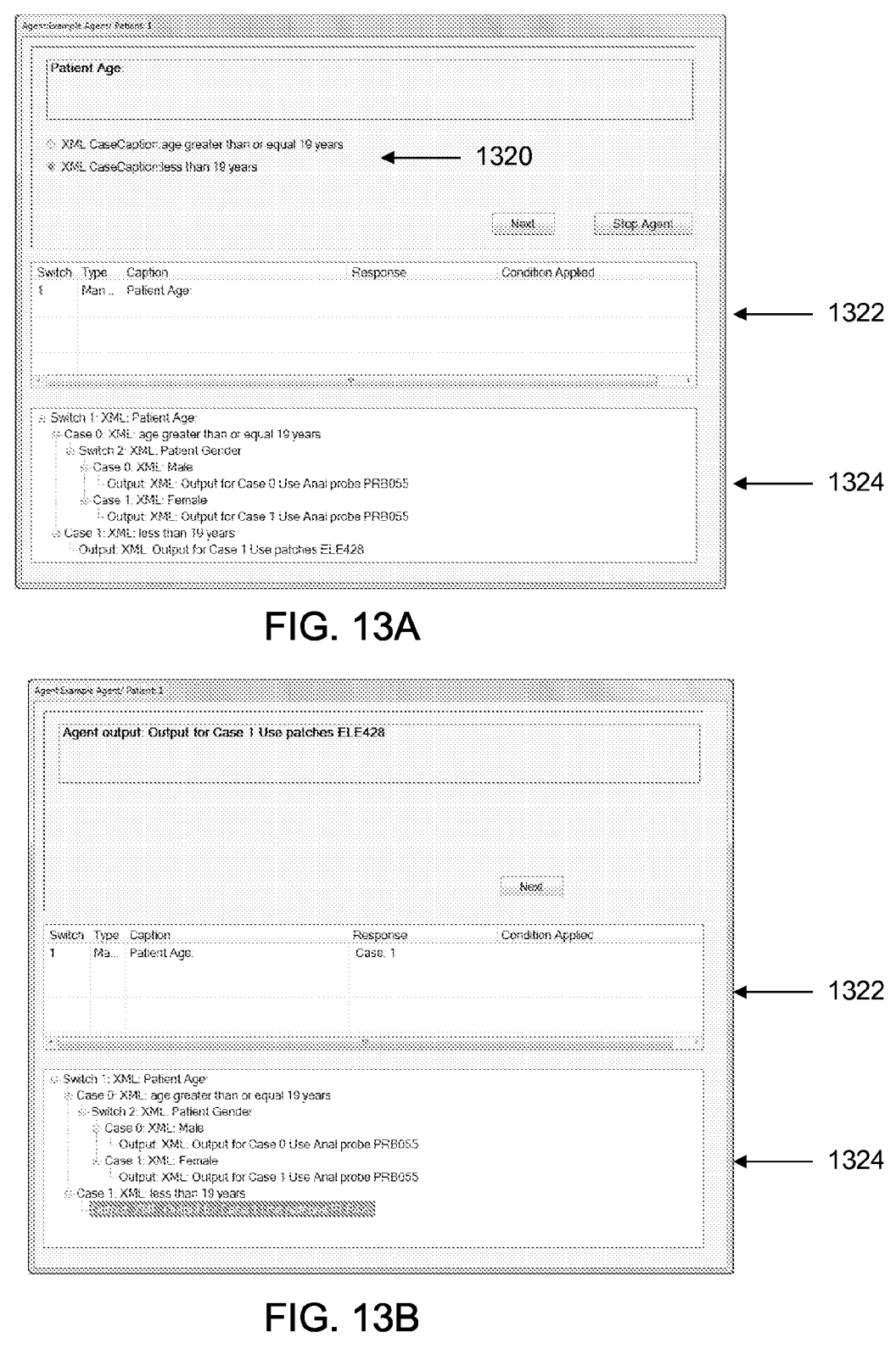
Figure 13C:
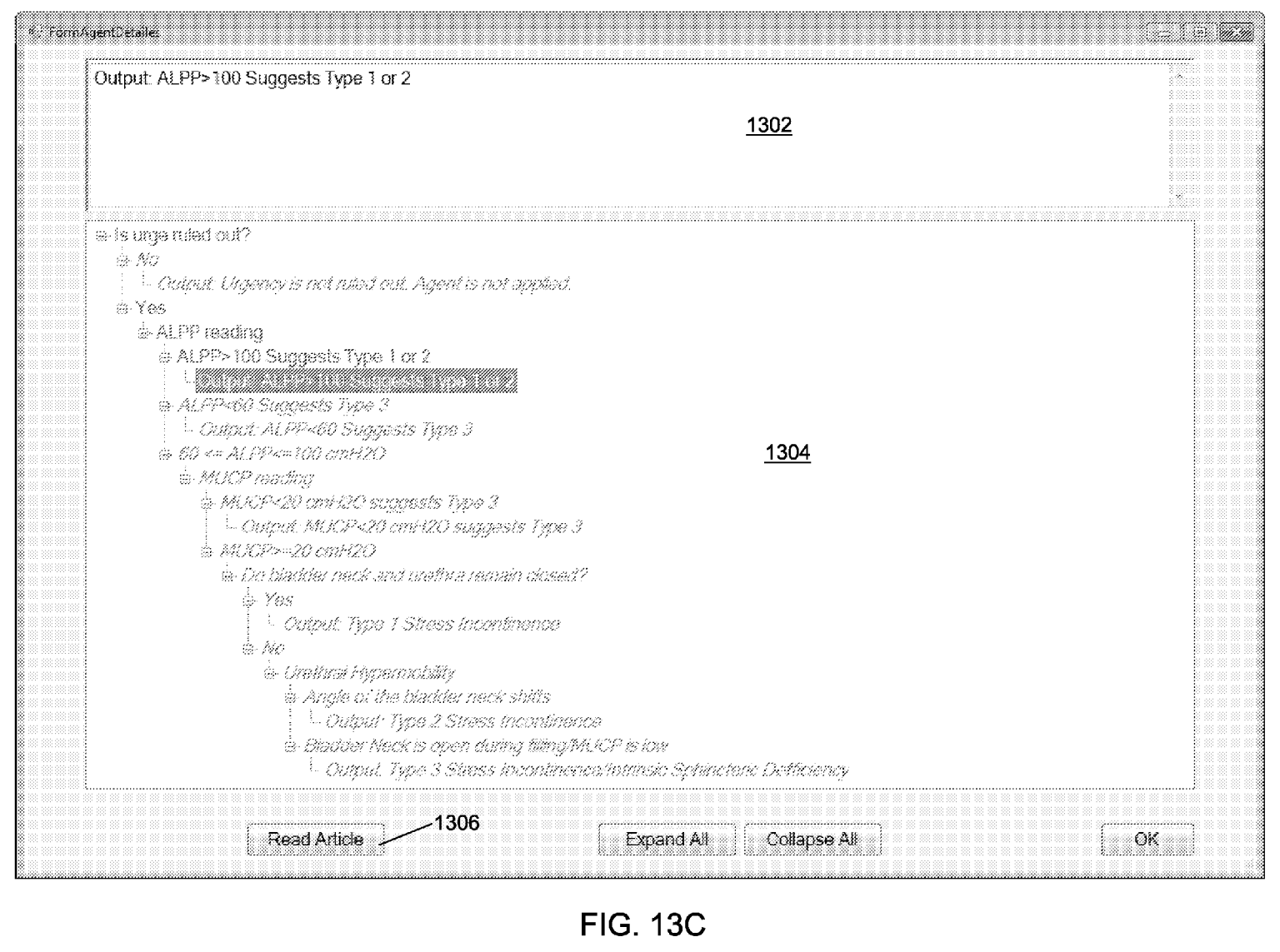

FIG. 12 illustrates two examples of trigger points for agents that include event triggers and polling triggers. Examples of things that can be event triggers includes e-mail/messaging triggers, input conditions be completed and/or information needed for a particular input is provided, date/time events such as a certain amount of time has passed and that time lapse has value as an input for an agent, and manual invocation/debug mode. The manual invocation/debug mode can be used if the professional would like to see how the inputs impact the outputs to gain a better understanding or if there is a particular agent that is of interest, then the professional can interact with just that agent to minimize the amount of information needed to be gathered/entered into the agent to obtain an output. FIGS. 13A-13C provide examples of an interface that illustrates examples of the manual invocation/debug mode according to the invention in the medical urological field. In at least one embodiment, the manual invocation/debug mode allows the professional to confirm the data and/or override the data to more accurately reflect the situation. The illustrated example of a polling trigger is to set individual input based on date or time. Additional examples regarding polling triggers have been discussed earlier in this disclosure.

In a further embodiment, when the professional overrides an agent's output by changing a switch. The system will update the agent for use by that professional (and anyone else selected by the professional such as other people in the same medical/legal office or department) to reflect the updated switch. An annotation will be added to the meta tags of the change. An example of a change might be changing an age switch from 18 to 19 based on, for example, new literature or user experience. In at least one embodiment, the agent manager will inquire with the user the basis for the change so that a record can be made.

FIG. 12 identifies a system rule as including relationships. In at least one embodiment, an example of a relationship is whether there are other agents that have a similar application including ones that provide different outputs and reach contrary conclusions. In another embodiment, the relationship provides the connection between all the inputs with the outputs. The relationships in at least one embodiment are used by the agent manager to organize the agents in a display interface such that agents analyzing similar data and/or designed to reach conclusions on similar scenarios are proximate to each other in the display interface.

FIG. 12 also identifies examples of the form of outputs for individual agents. Examples include displaying a dialog box message as part of the interface for the agent manager or as a popup message, e-mail or other messaging alerts, report elements for a database, trace logs and usage statistics, and decision explanations. The trace logs and usage statistics in at least one embodiment are used to order agents for use by the professional using the system, other professionals in the field, or to identify the agents being used most and that other professionals may want to adopt. Conversely, this information in at least one embodiment is used to identify agents that may have a technical issue or be viewed as having less value to the profession. The decision explanations as an output in at least one embodiment will provide the user an explanation of the rationale behind the decision or output of the agent that can be used to confirm the decision by the user and/or to educate the user.

FIGS. 13A and 13B illustrate two example interfaces for viewing the underlying rules used by an agent. Both figures use the example agent illustrated in FIG. 14A with patient 1. FIG. 13A illustrates how an user is able to progress through the agent's processing one switch at a time with the first step being illustrated in the figure with the two options available (i.e., age greater than or equal 19 years and less than 19 years) with two buttons available 1320. The Next button advancing the agent to the next step based on the selection made with the radio buttons and the Stop Agent button will exit the interface. The progress section 1322 shows what inputs have been received and processed by the agent. The rule section 1324 lists the switches and cases that make up the particular agent.

FIG. 13B illustrates the interface after the answer of "less than 19 years" was selected in FIG. 13B. The progress section 1322 shows that the Response was "Case: 1" while the rule section 1324 shows the "Case 1: XML:less than 19 years" results in an output of "for Case 1 Use patches ELE428". The output is also provided at the top of the interface in the illustrated interface.

FIGS. 14A and 14B illustrate examples of agents as .xml files (although other formats/languages can be used), the outputs, and the switches used in each agent to produce the output. In FIG. 14A, the switches (<Switch Switch Caption= . . . >) are the portions of the agents that require information for a decision to be made that may lead to further decisions and/or an output for the agent based on a rule. In the illustrated example of FIG. 14A, the two pieces of data needed for inputs are the patient's age and sex. Based on the inputs, three outputs are possible based on the three rules in the illustrated agent in FIG. 14A. But as illustrated in this example, if the patient is under the age of 19 years, then an output can be provided irrespective of the sex of the patient. In a scenario where the agent is set to run upon entry of a trigger, then once the age is entered the agent will provided an output if the patient is under 19 years old even if the patient's sex has not been entered assuming the agent is relevant for the reason for the patient's visit. As discussed previously and illustrated in the figures, the output could be to the agent manager for display or other use or entered into a database such as an electronic medical records system.

In another embodiment using the example agent of FIG. 14A as the discussion basis, would have the agent manager identify for the professional that the agent is missing the patient's sex before it is able to provide an output. This would occur where the patient's age is 19 years or older. The agent manager in at least one embodiment when no data is available for the agents in at least one embodiment would list or otherwise identify the inputs desired by the agents. As data and information is provided to the agents, updating the list to reflect the data or information provided or that has become unnecessary for an output to be provided by the agent.

In another embodiment, the agent manager provides information regarding any agent that is selected that shows which chain through the agent is being used (or possible), for example, graphically using color or other text formatting as illustrated in FIG. 13C. The illustrated interface in at least one embodiment is reached by selecting the agent in one of the illustrative interfaces shown in FIGS. 4 and 6-7B. The example interface illustrates an output section 1302 that shows the output as determined by the agent for the currently selected patient, a rule set section 1304 showing the triggers and switches, and a Read Article button 1306 for providing information about the source material or a link to where the material can be found. FIG. 13C also depicts an Expand All button, a Collapse All button, and an OK button. For data branches that are not applicable for the particular situation, the agent manager would show that chain graphically differently than the data branch being used such as grayed out compared to a color font or different font style (italics compared to normal). See section 1304. This display would be based on the progress of the agent and the data/information that has been provided to the agent to provide a real-time display. The illustrated interface provides an example of how a user could see the rules process for a particular situation to make a decision to modify it as discussed previously.

FIG. 14B illustrates another example agent according to at least one embodiment of the invention. The illustrated agent is named ALPP. The illustrated agent provides a more complicated example than that shown in FIG. 14A as there are more switches and branches that are followed depending upon the inputs that are received by the agent.

In a further embodiment, selecting an agent or moving the cursor proximate to the agent's name provides the user with information regarding the underlying source material used to create the agent. Examples of how the information may be provided include, for example, displaying a pop-up window with the citation or a link that will direct the user to the source material and opening the source material in another window or in software appropriate to view the material such as Adobe Acrobat. In at least one further embodiment there is an icon or a link associate with the agent that will be used to receive the request for additional material.

In at least one embodiment the agent manager will sort the available agents based on a variety of parameters. Examples of those parameters include a certain author being present, publication or creation dates, titles of source material or agents, agents created by a predefined group such as customers of a particular company or members of a group/association, application (or relevancy of) for the agent, and user favorites and/or rankings. In addition to the sorting function, the agent manager in a further embodiment will include the ability to search the agents for example by using the meta tags.

The agents used in the system as mentioned previously can be based on a variety of sources of information. As such, one distribution method for the agents according to the invention is as follows. Agents in at least one embodiment are prepared based on reviews of literature and other material from the field. Based on findings, instructions, and similar information, a set of rules is created that includes identification of inputs and switches that are discussed in the information source to reach the output described in the information source. The agents then could be provided to customers through a subscription basis, sold individually or in groups a la carte, and by the use. The variety of described data and metrics that in different embodiments is gathered can be used to organize the agents and present the agents to the customers. Additional metrics that are used in other embodiments include popularity based on, for example, uses or downloads; technical area; cost; user ratings and/or reviews; etc. The popularity could be combined with technical area and/or geographic location of the user. An example is displaying agents for urology would be displayed for urologists but probably not oncologists unless there was an overlap across disciplines. Another technical example is displaying agents based on $4^{th}$ Circuit case law for attorneys practicing in the $4^{th}$ Circuit. A geographic location example is displaying agents based on Canadian medical practices and regulations to Canadian doctors but not U.S. doctors.

Figure 15:
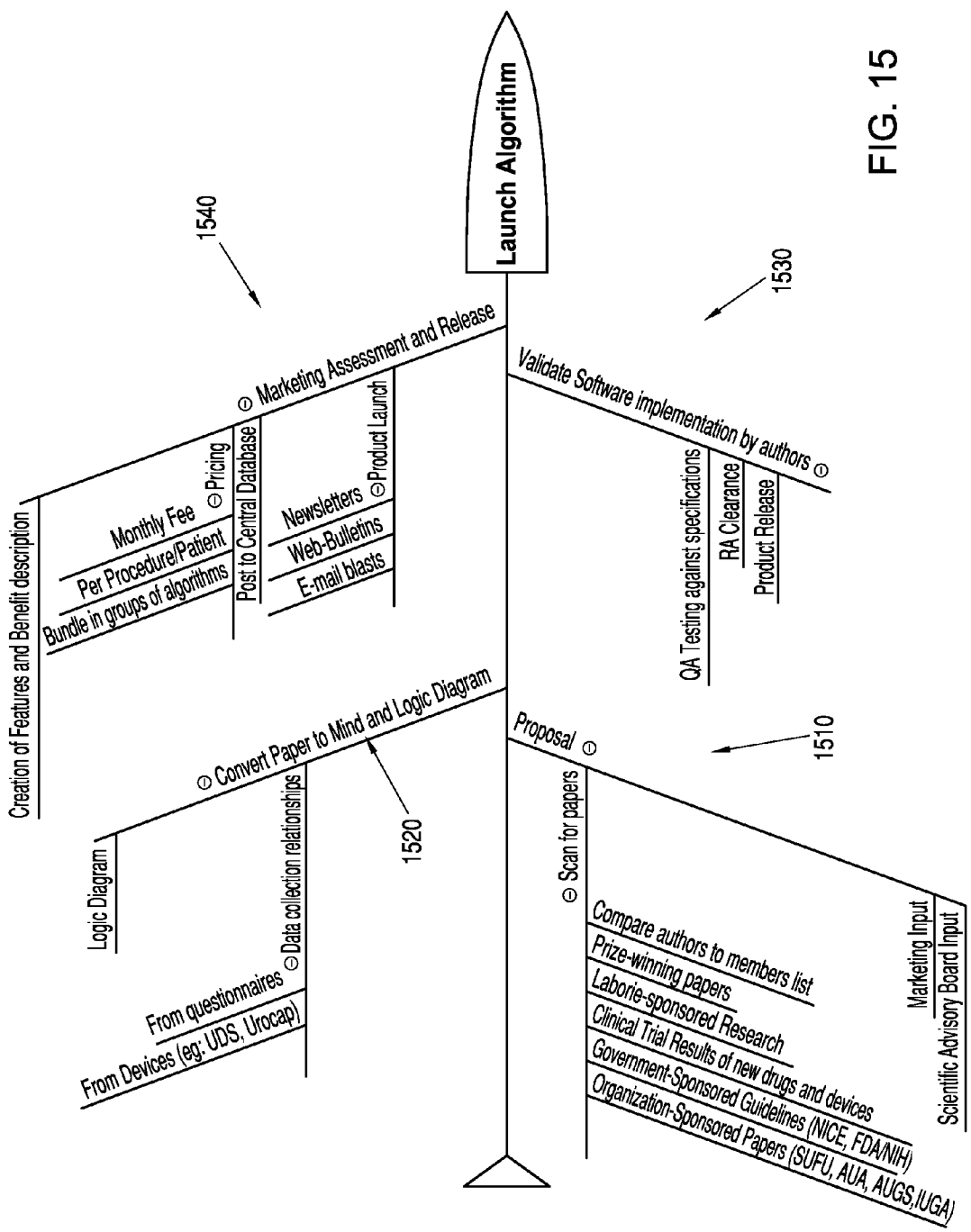
FIG. 15 illustrates a representation of the process for development of agents according to an embodiment of the invention.

FIG. 15 illustrates a workflow for development of individual agents that includes the proposal stage 1510, the conversion of the material to a logic diagram stage 1520, the validation stage 1530, and the marketing stage 1540. Based on this disclosure, it should be appreciated that one or more stages (e.g., the marketing stage) illustrated in FIG. 15 may be omitted including any subparts of the stages.

The illustrated proposal stage 1510 is illustrative of examples of sources of material that can be used to develop agents including articles or papers, marketing department input, and a scientific advisory board input. The articles or papers may be located from a variety of places including author searches to locate subscribers/purchasers of agents or leading individuals in the field; prize-winning papers; sponsored research by corporations or government entities; clinical trial results of new drugs and devices in the medical field; government sponsored guidelines such as guidelines propagated by NICE, FDA, and NIH; organization sponsored papers; and articles or papers appearing in certain journals or being included in certain conferences. The marketing department may provide insight into agents that would be of interest to potential users. The scientific advisory board in at least one embodiment would include leading individuals in the field that develop agent logic separate and in addition to other sources. In another embodiment, the advisory board provides leads and/or insights into forthcoming developments in the field.

Figure 16:
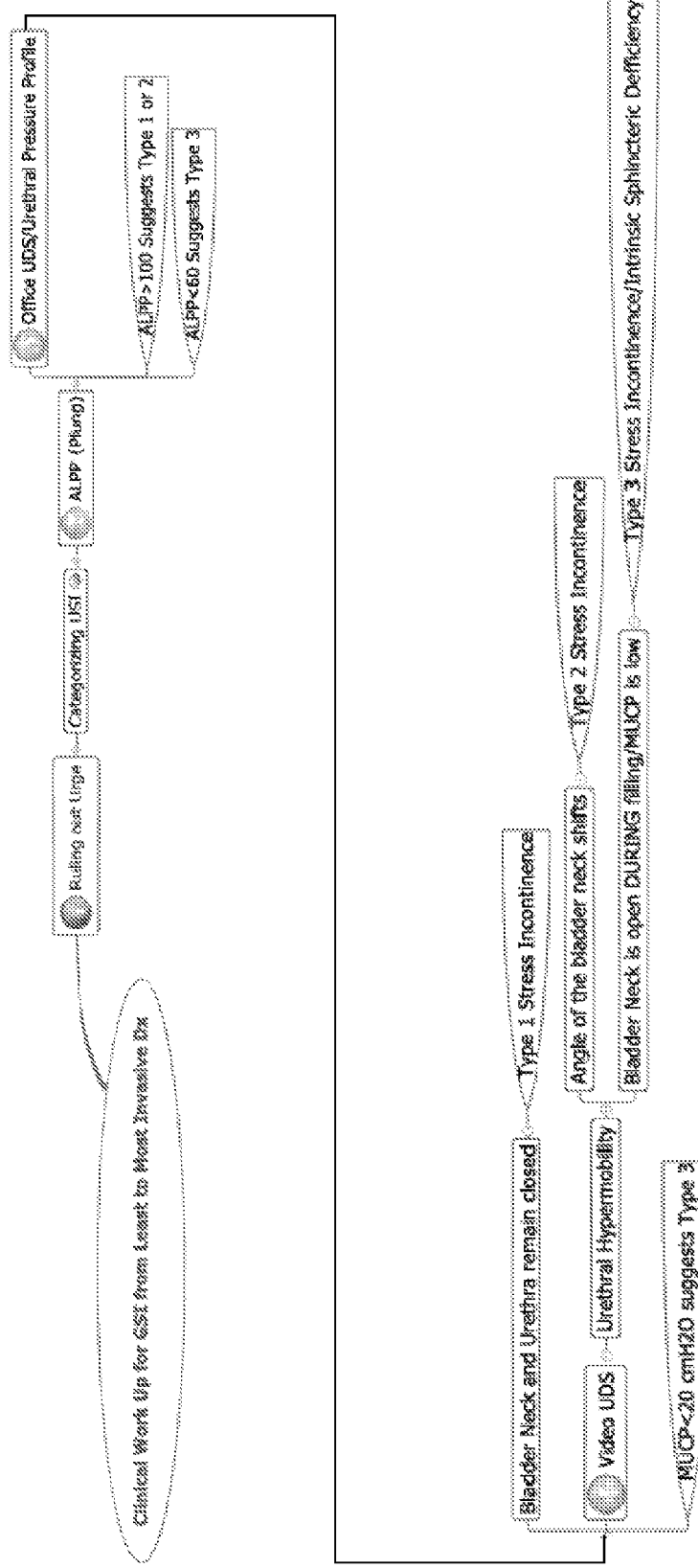
FIG. 16 illustrates an example of the logic flow of an example agent according to at least one embodiment of the invention.

The conversion stage 1520 in at least one embodiment includes the creation of a logic diagram from the contents of the source material that shows the information beneficial as inputs and the type of output that would be provided. Examples of outputs include a score, a numerical or other representation of a condition, a diagnosis, a recommendation for additional questions or testing, and one or more probabilities for certain things to exist. The inputs represent the data collected that will be related to the output(s). Sources of data as illustrated in FIG. 15 include, for example, from devices such as UDS or Urocap in the urological field, and questionnaires or questions. Another criterion that is included in at least one embodiment is the problem or issue that the agent is created for use. Additional sources may come from pulling (or receiving) data from an electronic medical records system. FIG. 16 illustrates an example of a logic diagram for an agent to assist the user in determining the clinical work up for Genuine Stress Incontinence (GSI) from least to most invasive testing. As the user progresses through the logic diagram that in at least one embodiment is implemented as a questionnaire that asks questions to gather the information to serve as inputs for this particular agent.

The validation stage 1520 illustrated in FIG. 15 includes quality assurance testing for verifying the specifications (e.g., if the program outputs meet the requirements of inputs) including the data from the published article (or other source), regulatory clearance (if needed), clinical evaluation testing (if needed) and final product release to market.

The launch of an agent or collection of agents 1540 can take a variety of forms that in part is dependent upon the pricing model used as illustrated in FIG. 15. In one embodiment, the agent is posted (or loaded) into a central database for purchase or downloading by customers. In another embodiment, the agent is provided as part of an application service provider arrangement. In another embodiment, written material regarding the agent is created discussing the features and benefits. In a further embodiment, the agent is launched using such marketing tools as e-mail, websites, newsletters, and press releases.

Figure 17:
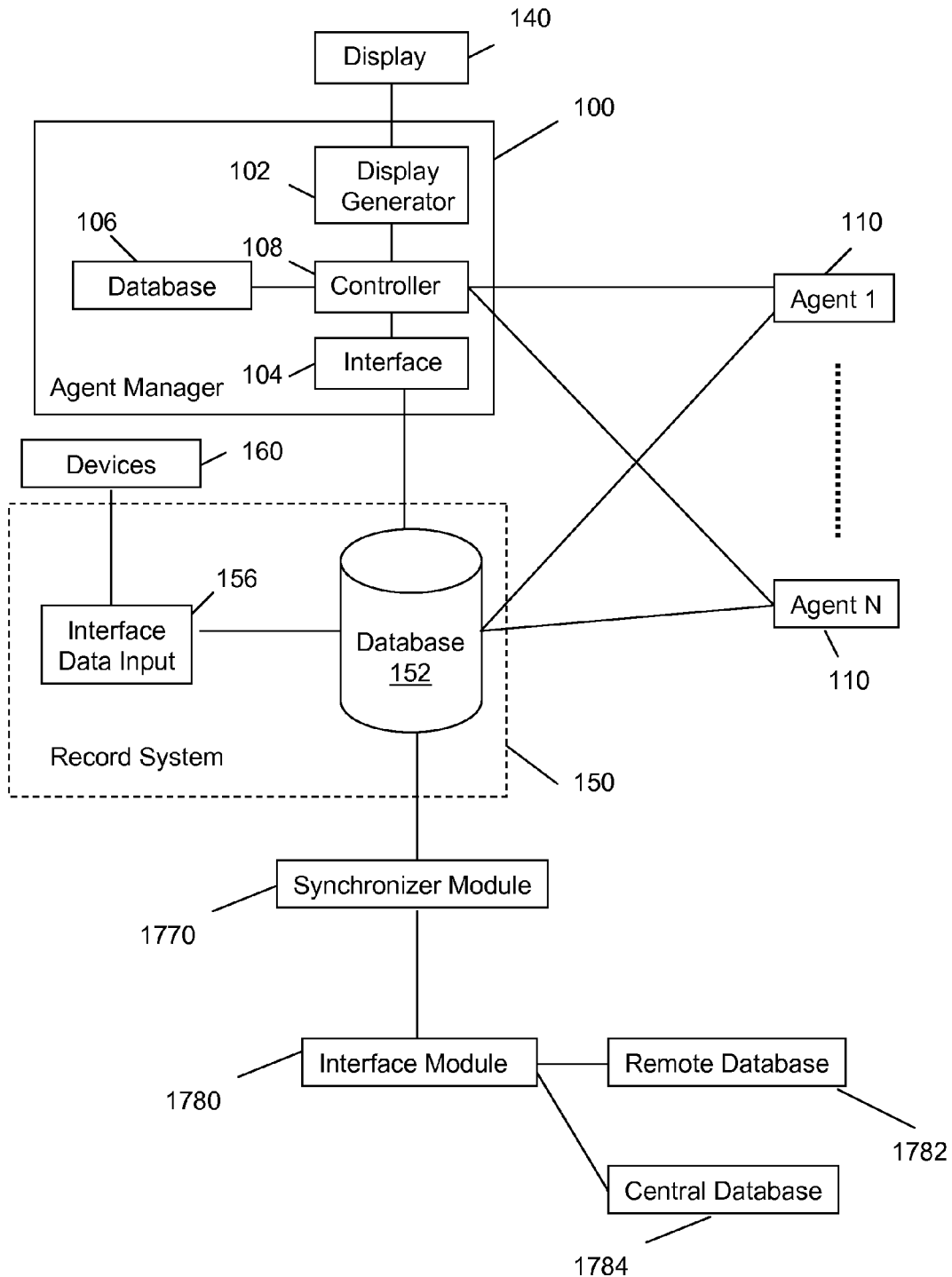
FIG. 17 illustrates a block diagram according to another embodiment of the invention.

FIG. 17 illustrates another embodiment according to the invention. The illustrated embodiment adds a synchronizer module 1770 connected to the record system and a set of remote components in different embodiments provide, for example, including but not limited to backup, remote access, update, etc. The remote components include an interface module 1780, a remote database 1782, and a central database 1784. Although the synchronizer module 1770 is illustrated as being separate from the record system 150, in at least one embodiment the synchronizer module 1770 is incorporated into the record system 150. In a further embodiment, the synchronizer module 1770, the record system 150, and the agent manager 100 are integrated together.

The synchronizer module 1770 in at least one embodiment provides for backup of the data present in the database 152 to the remote database 1782 through the interface module 1780, which in at least one embodiment assigns a code to each data entry received from the database 152 so that the remote database 1782 includes the original data plus an identifier of who (e.g., user, location, facility, company, individual, etc.) owns the data. The remote database 1782 in at least one embodiment provides for remote access through the interface module 1780 to the data contained in the database 152 to users that are traveling including the ability to run agents. In at least one embodiment, the interface module 1780 controls access by users to the remote database 1782 based at least in part on whether the user is affiliated with the data in the remote database 1782. The affiliation is determined at least in part on whether the user has been granted permission by the source of the data to access the data remotely where the determination uses the identifier of who owns the data added to the data by the interface module 1780 when the data was loaded into the remote database 1782, which is useful in an implementation where there are multiple doctor offices' whose data is present in the remote database to avoid access to data from other doctor offices by users.

In a further embodiment, the synchronizer module 1770 performs checks with the interface module 1780 to see if the central database 1784 has any new or modified agents to be downloaded to the local system and what adjustments are needed in any database present in the agent manager 100 to reflect the new or modified agents. In at least one embodiment, the synchronizer module 1770 communicates directly with the central database 1784 without the presence of the interface module 1780. The synchronizer module 1770 depending upon the implementation may be continually in contact with the interface module 1780, the remote database 1782 and/or central database 1784 to facilitate substantially real-time updating and/or backing up of data, be set to perform its function at predetermined time periods or intervals, or upon manual request by a user. In a further embodiment, the interface module 1780, the remote database 1782 and/or the central database 1784 are implemented using cloud technology. In at least one embodiment, the remote database 1782 contains data for just one office or practice, which allows for omission of the identifier of the owner of the data to be added by the interface module 1780.

Figure 18:
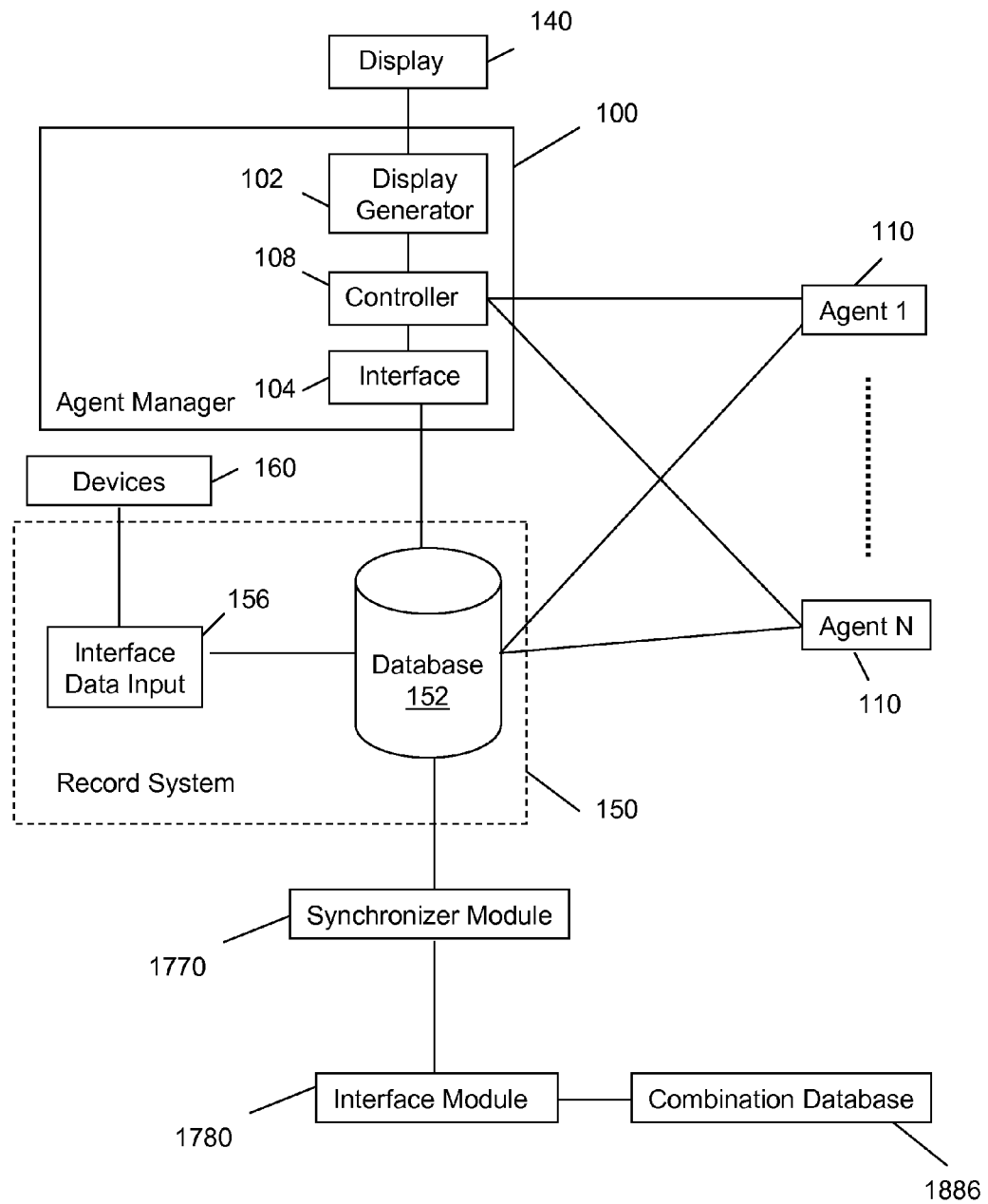
FIG. 18 illustrates another block diagram according to another embodiment of the invention.

FIG. 18 is similar to FIG. 17 with the exception that the remote database 1782 and the central database 1784 are combined into one database 1886. FIG. 18 also illustrates an alternative embodiment that omits the agent database 106 from the agent manager 100.

An alternative embodiment to any of the embodiments discussed in the previous two paragraphs, is for the interface module 1780 to push updates of software and/or agents to the synchronizer module 1770 on, for example, a predetermined schedule or as they become available. In a further alternative embodiment, the interface module 1780 pulls any updated data from the database 152 to the remote database 1782 or combination database 1886 on a predetermined schedule.

In a further embodiment, when a new agent or modified agent is added to the system, the agent runs for a preselected grouping of patients that can be based upon, for example, condition/situation of the patient or person, temporal configuration for any situation analyzed in the preceding predetermined amount of time, or the last N number of situations analyzed by the system where N is any positive integer.

As will be appreciated by one skilled in the art based on this disclosure, aspects of the present invention may be embodied as a system, method or computer program product. Accordingly, aspects of the present invention may take the form of an entirely hardware embodiment, a processor operating with software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Computer program code for carrying out operations for aspects of the present invention may be written in any combination of one or more programming languages, including an object oriented programming language such as Java, Smalltalk, C++, C#, Transact-SQL, XML, or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute with the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 19:
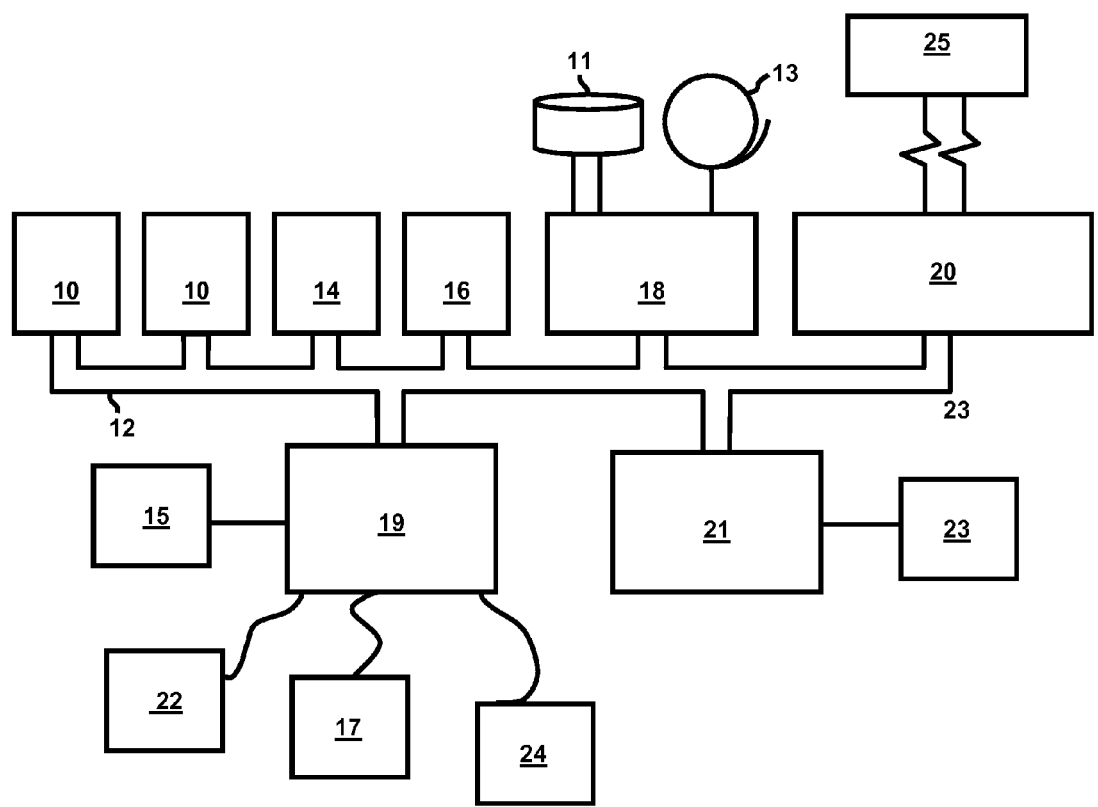
FIG. 19 illustrates a computer program product and computer implementation according to an embodiment of the invention.

Referring now to FIG. 19, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 10. The CPUs 10 are interconnected with system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of at least one embodiment of the invention. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

Although the present invention has been described in terms of particular example embodiments, it is not limited to those embodiments. The embodiments, examples, and modifications which would still be encompassed by the invention may be made by those skilled in the art, particularly in light of the foregoing teachings.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

Those skilled in the art will appreciate that various adaptations and modifications of the exemplary and alternative embodiments described above can be configured without departing from the scope and spirit of the invention. Therefore, it is to be understood that, within the scope of the appended claims, the invention may be practiced other than as specifically described herein.

The invention claimed is:

1. A system comprising:
    an agent manager having
        an interface for interacting with at least one external database,
        an internal database, and
        a controller connected to said interface and said internal database; and
    a plurality of agents in communication with said agent manager, each agent having a plurality of flow steps for processing information substantially in parallel with the other agents to provide an output to at least one of said agent manager and an agent database interface for communicating with at least one external database, the output is based on at least one input by said agent; and
    wherein said internal database of said agent manager includes an entry for each agent in communication with said agent manager,
    each entry in said internal database includes a technical area for each agent,
    said controller controls the flow of information from said interface to said plurality of agents based at least on the technical area of each agent in said internal database.

2. The system according to claim 1, wherein said controller publishes all information received through said interface to all agents in communication with said agent manager.

3. The system according to claim 1, wherein said agent manager further includes a display generator,
    said display generator creates a graphical user interface for displaying any output received from agents in communication with said agent manager.

4. The system according to claim 3, wherein said controller monitors the operation of the agents and provides this information to said display generator for display.

5. The system according to claim 1, wherein said interface monitors the availability of data in any database in communication with said interface.

6. The system according to claim 5, wherein said controller publishes data as it becomes available in any connected external database.

7. The system according to claim 1, wherein said interface monitors any connected external database in communication with said interface for predetermined events before pulling data for publication by said controller to any agents in communication with said agent manager.

8. The system according to claim 1, further comprising an electronic medical record system having at least one of said at least one external databases interacting with said interface.

9. The system according to claim 1, wherein the flow steps are based on at least one publication.

10. A system comprising:
    an agent manager having
        an interface for interacting with at least one external database,
        an internal database, and
        a controller connected to said interface and said internal database; and
    a plurality of agents in communication with said agent manager, each agent having
        an agent database interface for communicating with said internal database of said agent manager, and
        a plurality of flow steps for processing information substantially in parallel with the other agents to provide an output to said agent database interface where the output is based on at least one input and the flow steps are based on at least one publication; and
    wherein said internal database of said agent manager includes an entry for each agent in communication with said agent manager,
    each entry in said internal database includes a technical area for each agent,
    said controller controls the flow of information from said interface to said plurality of agents based at least on the technical area of each agent in said internal database.

11. The system according to claim 10, wherein said controller publishes all information received through said interface to all agents in communication with said agent manager.

12. The system according to claim 10, wherein said agent manager further includes a display generator,
    said display generator creates a graphical user interface for displaying any output received from agents in communication with said agent manager, and
    said controller monitors the operation of the agents and provides this information to said display generator for display.

13. The system according to claim 10, wherein said interface monitors the availability of data in any database in communication with said interface, and
said controller publishes data as it becomes available in any connected external database.

14. The system according to claim 10, wherein said interface monitors any connected external database in communication with said interface for predetermined events before pulling data for publication by said controller to any agents in communication with said agent manager.

15. The system according to claim 10, further comprising an electronic medical record system having at least one of said at least one external databases interacting with said database interface of each agent.

16. A system comprising:
an agent manager having
an interface for interacting with at least one external database,
an internal database, and
a controller connected to said interface and said internal database; and
a plurality of agents in communication with said agent manager, each agent having a plurality of flow steps for processing information substantially in parallel with the other agents to provide an output to said agent manager, the output is based on at least one input by said agent, and
an electronic medical record system having at least one records database in communication with at least one of said interface of said agent manger and said plurality of agents; and
wherein said internal database of said agent manager includes an entry for each agent in communication with said agent manager, and
each entry in said internal database includes a technical area for each agent,
said controller controls the flow of information from said interface to said plurality of agents based at least on the technical area of each agent in said internal database.

17. The system according to claim 16, wherein said agent manager further includes a display generator,
said display generator creates a graphical user interface for displaying any output received from agents in communication with said agent manager, and
said controller monitors the operation of the agents and provides this information to said display generator for display.

18. The system according to claim 16, wherein said interface monitors the availability of data in any database in communication with said interface, and
said controller publishes data as it becomes available in any connected external database.

19. The system according to claim 16, wherein the flow steps are based on at least one publication.

\* \* \* \* \*